United States Patent
Bush, Jr. et al.

(10) Patent No.: US 9,351,775 B2
(45) Date of Patent: *May 31, 2016

(54) CERVICAL PLATE WITH A FEEDBACK DEVICE FOR SELECTIVE ASSOCIATION WITH BONE SCREW BLOCKING MECHANISM

(71) Applicant: Stryker European Holdings I, LLC, Kalamazoo, MI (US)

(72) Inventors: Charles L. Bush, Jr., Fairfield, NJ (US); Hanspeter Robert Bayer, Meriden, CT (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,738

(22) Filed: Nov. 7, 2014

(65) Prior Publication Data

US 2015/0066096 A1    Mar. 5, 2015

Related U.S. Application Data

(63) Continuation of application No. 12/291,335, filed on Nov. 7, 2008, now Pat. No. 8,906,077.

(60) Provisional application No. 61/002,486, filed on Nov. 9, 2007.

(51) Int. Cl.
*A61B 17/58* (2006.01)
*A61B 17/80* (2006.01)
(Continued)

(52) U.S. Cl.
CPC ......... *A61B 17/8042* (2013.01); *A61B 17/8615* (2013.01); *A61B 17/888* (2013.01); *A61B 17/8888* (2013.01); *A61B 17/808* (2013.01); *A61B 2019/444* (2013.01)

(58) Field of Classification Search
CPC ............... A61B 17/80; A61B 17/8033; A61B 17/8042; A61B 17/8047
See application file for complete search history.

(56) References Cited

U.S. PATENT DOCUMENTS

| | | |
|---|---|---|
| 5,876,402 A | 3/1999 | Errico et al. |
| 5,931,838 A | 8/1999 | Vito |

(Continued)

OTHER PUBLICATIONS

International Search Report for Application No. PCT/US2008/12668 dated Jan. 12, 2009.

(Continued)

*Primary Examiner* — Matthew Lawson
(74) *Attorney, Agent, or Firm* — Lerner, David, Littenberg, Krumholz & Mentlik, LLP

(57) ABSTRACT

A bone plate having at least one screw hole adapted to receive a bone screw, a blocker having a blocking end for blocking a bone screw from further backout of bone the blocker being predisposed in a blocking position wherein the blocking end at least partially overlaps a portion of the screw hole, the blocker being moveable from the blocking position by contact with the bone screw during insertion of the bone screw into the screw hole, and a blocker fixation element having an open orientation at which the blocker can move from the blocking position and a closed orientation preventing substantial movement of the blocker from the blocking position. The blocker fixation element cannot be moved to the closed orientation unless the screw head passes the blocker, thereby revealing that the blocker fixation element is in position to prevent substantial movement of the blocker.

16 Claims, 20 Drawing Sheets

(51) Int. Cl.
*A61B 17/86* (2006.01)
*A61B 17/88* (2006.01)
*A61B 19/00* (2006.01)

(56) References Cited

U.S. PATENT DOCUMENTS

| | | | |
|---|---|---|---|
| 6,139,550 A | 10/2000 | Michelson | |
| 6,258,089 B1 | 7/2001 | Campbell et al. | |
| 6,261,291 B1 | 7/2001 | Talaber et al. | |
| 6,599,290 B2 | 7/2003 | Bailey et al. | |
| 6,602,255 B1 | 8/2003 | Campbell et al. | |
| 6,702,817 B2 | 3/2004 | Beger et al. | |
| 6,755,833 B1 | 6/2004 | Paul et al. | |
| 7,008,426 B2 | 3/2006 | Paul | |
| 7,070,599 B2 | 7/2006 | Paul | |
| 7,077,843 B2 | 7/2006 | Thramann et al. | |
| 7,204,837 B2 | 4/2007 | Paul | |
| 7,255,699 B2 | 8/2007 | Paul | |
| 7,481,811 B2 | 1/2009 | Suh | |
| 7,727,265 B2 | 6/2010 | Paul | |
| 7,740,649 B2 | 6/2010 | Mosca et al. | |
| 7,857,839 B2 | 12/2010 | Duong et al. | |
| 7,909,859 B2 | 3/2011 | Mosca et al. | |
| 7,909,860 B2 | 3/2011 | Rathbun et al. | |
| 8,002,809 B2 | 8/2011 | Baynham | |
| 8,016,864 B2 | 9/2011 | Assaker et al. | |
| 8,906,077 B2 * | 12/2014 | Bush et al. | 606/296 |
| 2003/0225409 A1 | 12/2003 | Freid et al. | |
| 2004/0030338 A1 | 2/2004 | Paul | |
| 2004/0034354 A1 | 2/2004 | Paul | |
| 2004/0097940 A1 | 5/2004 | Paul | |
| 2004/0127899 A1 | 7/2004 | Konieczynski et al. | |
| 2004/0127900 A1 | 7/2004 | Konieczynski et al. | |
| 2004/0127904 A1 | 7/2004 | Konieczynski et al. | |
| 2004/0153069 A1 | 8/2004 | Paul | |
| 2005/0021032 A1 | 1/2005 | Koo | |
| 2005/0049593 A1 * | 3/2005 | Duong et al. | 606/69 |
| 2005/0049595 A1 | 3/2005 | Suh et al. | |
| 2005/0071006 A1 * | 3/2005 | Kirschman | 623/17.11 |
| 2005/0071008 A1 | 3/2005 | Kirschman | |
| 2005/0096657 A1 | 5/2005 | Autericque et al. | |
| 2005/0177160 A1 | 8/2005 | Baynham et al. | |
| 2005/0234455 A1 | 10/2005 | Binder et al. | |
| 2005/0261690 A1 * | 11/2005 | Binder et al. | 606/69 |
| 2005/0283152 A1 | 12/2005 | Lindemann et al. | |
| 2006/0142768 A1 | 6/2006 | Paul | |
| 2006/0149255 A1 | 7/2006 | Doubler et al. | |
| 2006/0161157 A1 | 7/2006 | Mosca et al. | |
| 2006/0195100 A1 | 8/2006 | Kirschman | |
| 2006/0200146 A1 | 9/2006 | Doubler et al. | |
| 2006/0229620 A1 | 10/2006 | Rothman et al. | |
| 2006/0235398 A1 | 10/2006 | Farris et al. | |
| 2006/0235403 A1 * | 10/2006 | Blain | A61B 17/7059 606/249 |
| 2006/0241612 A1 | 10/2006 | Medoff | |
| 2007/0123884 A1 | 5/2007 | Abdou | |
| 2007/0233120 A1 | 10/2007 | Thramann et al. | |
| 2008/0287999 A1 | 11/2008 | Markworth | |
| 2009/0062863 A1 * | 3/2009 | Peppers | A61B 17/8038 606/289 |

OTHER PUBLICATIONS

European Extended Search Report for Application No. EP08848228 dated Oct. 15, 2012.

* cited by examiner

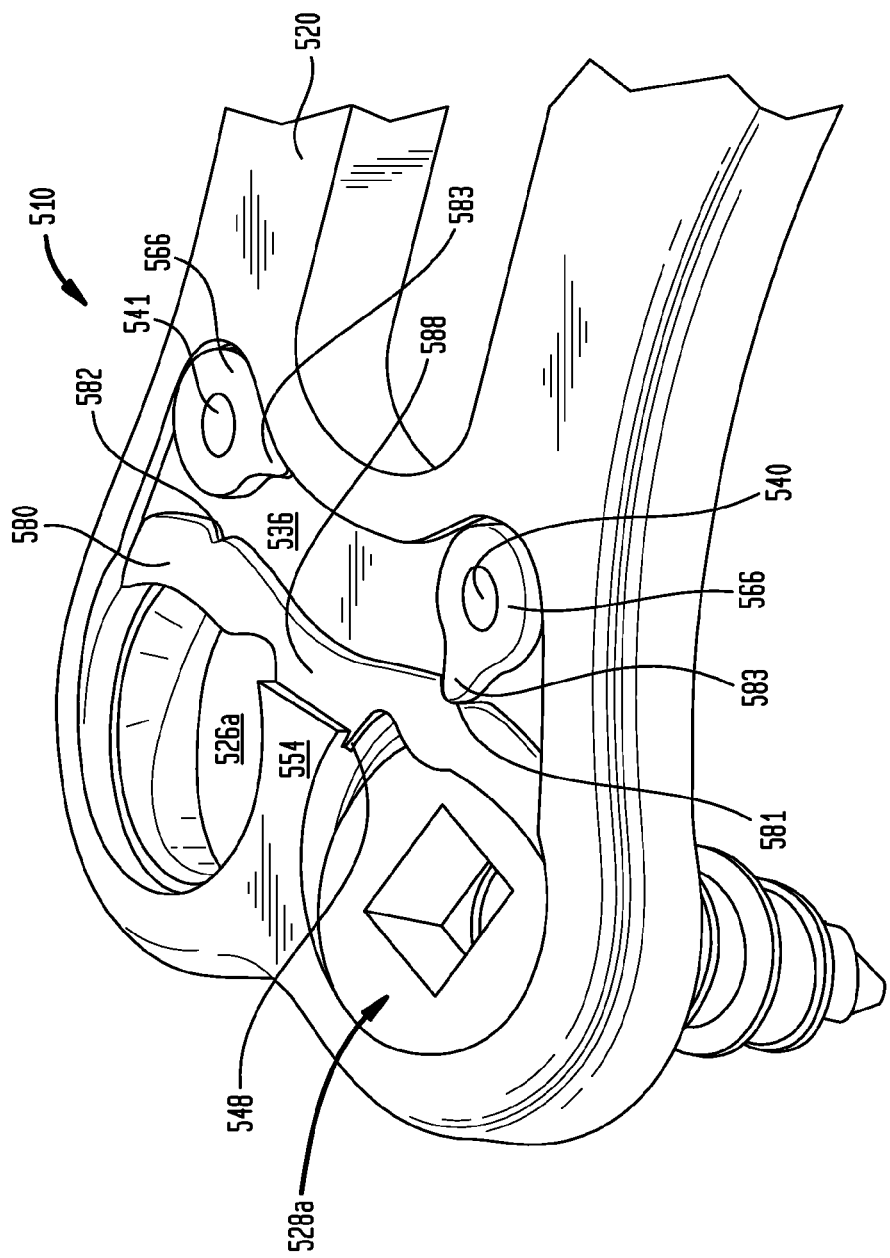

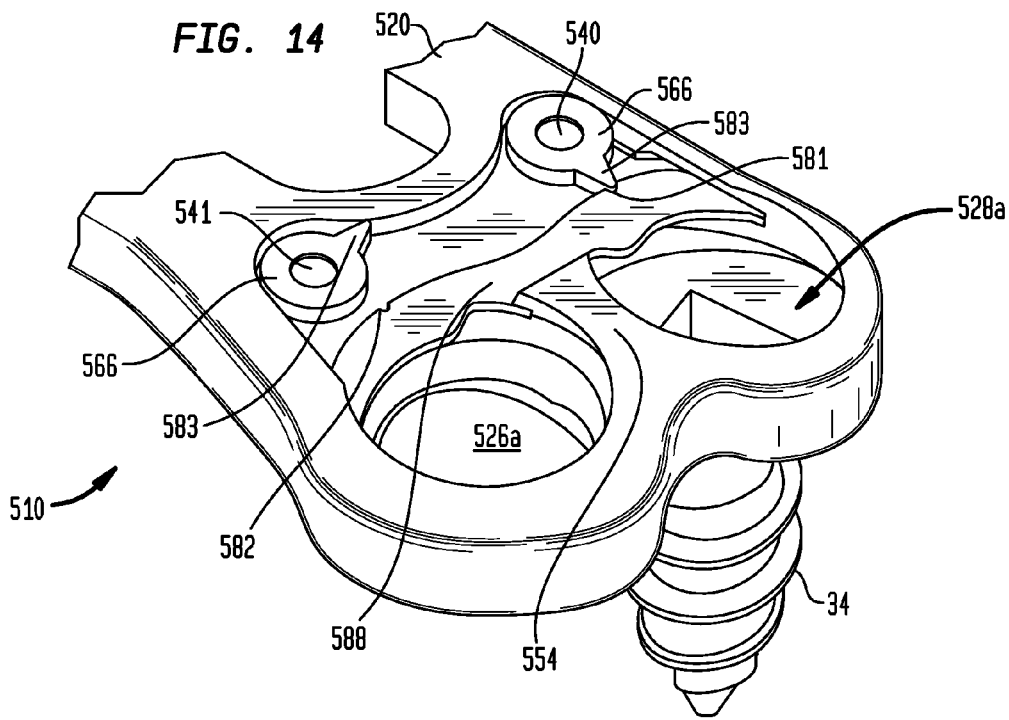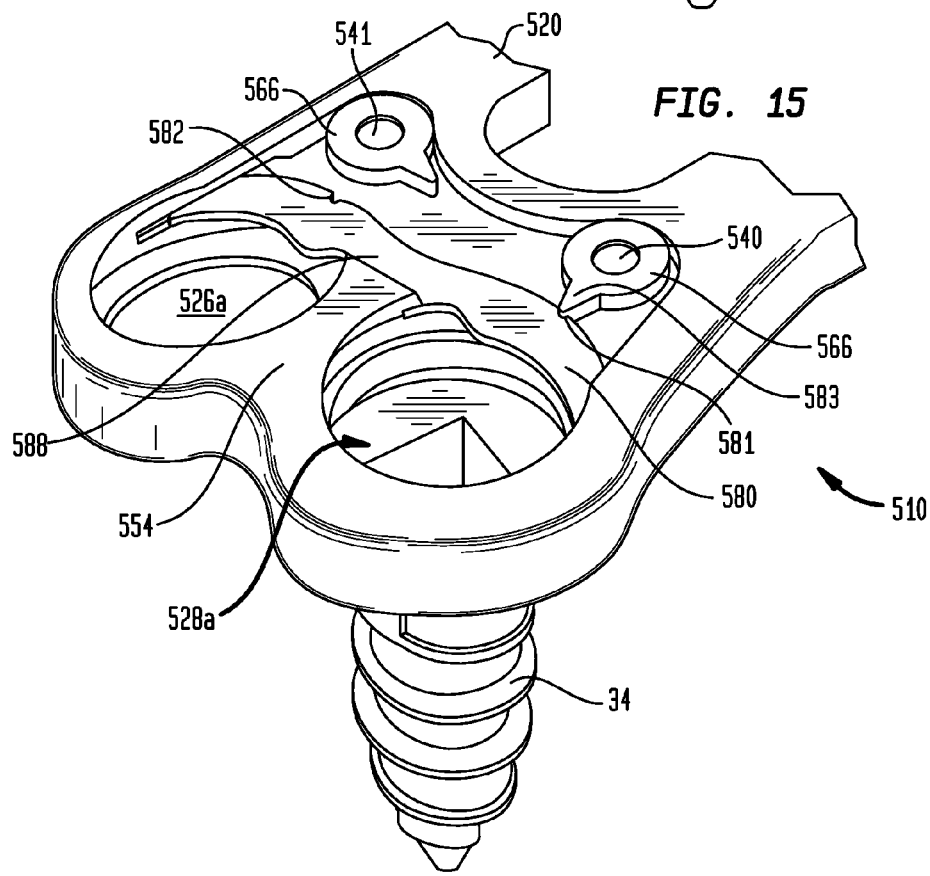

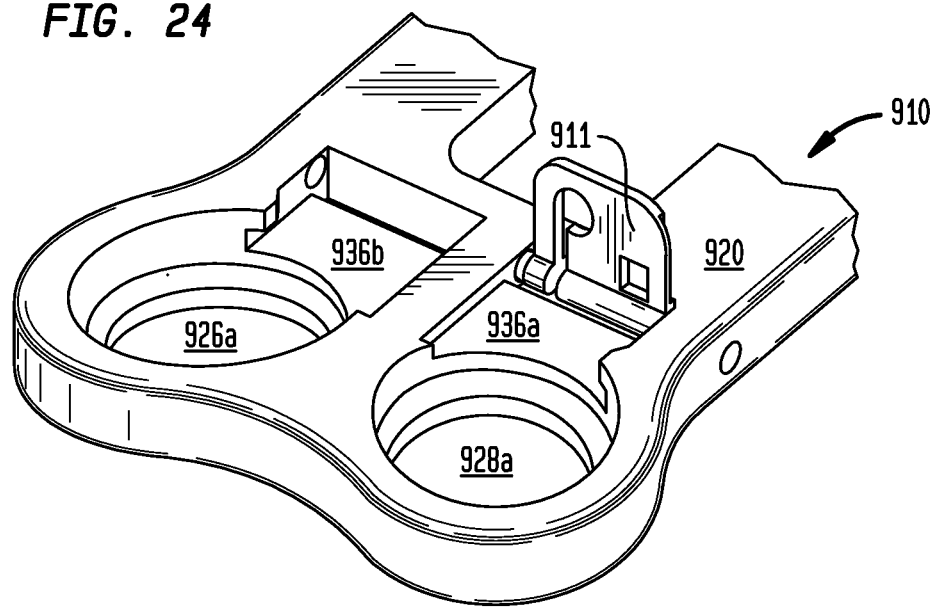
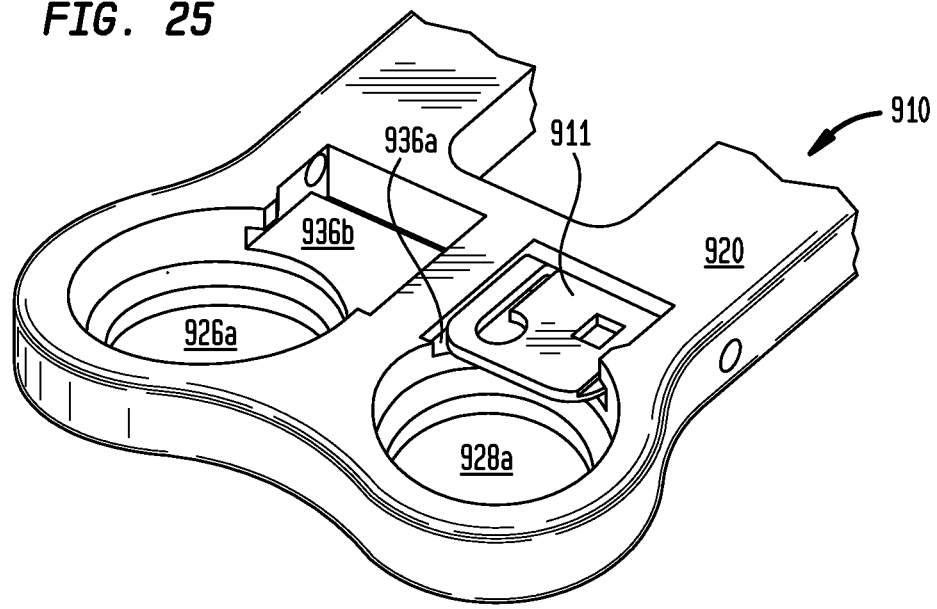

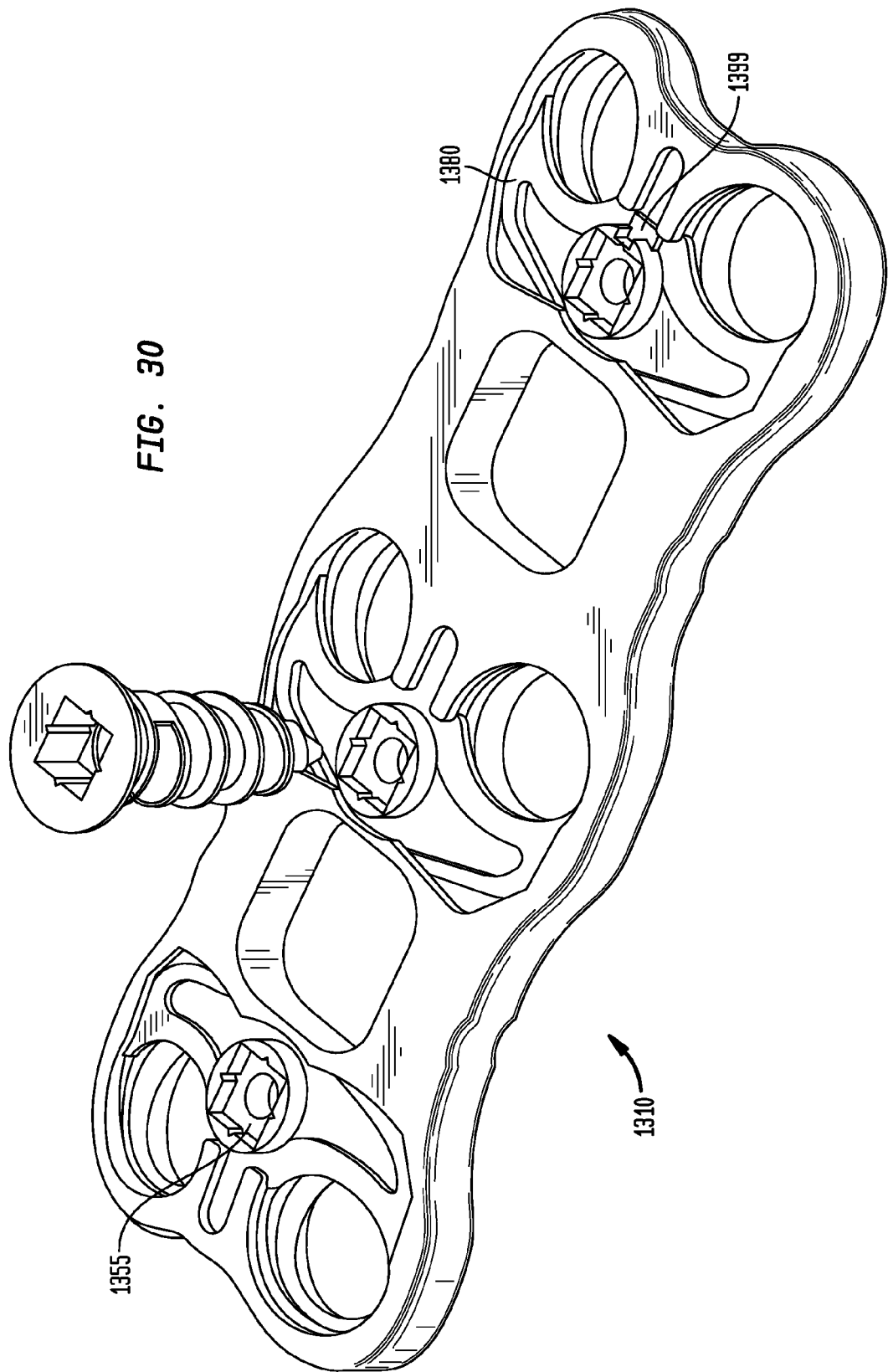

CERVICAL PLATE WITH A FEEDBACK DEVICE FOR SELECTIVE ASSOCIATION WITH BONE SCREW BLOCKING MECHANISM

CROSS-REFERENCE TO RELATED APPLICATIONS

This application is a continuation of U.S. patent application Ser. No. 12/291,335, filed on Nov. 7, 2008, which claims the benefit of the filing date of U.S. Provisional Patent Application No. 61/002,486, filed Nov. 9, 2007, and entitled "CERVICAL PLATE WITH A FEEDBACK DEVICE FOR SELECTIVE ASSOCIATION WITH BONE SCREW BLOCKING MECHANISM," the disclosures of which are hereby incorporated herein by reference.

BACKGROUND OF THE INVENTION

The present invention generally relates to a bone plate having a screw blocking mechanism. More particularly, the present invention relates to a cervical bone plate having a screw blocking mechanism that can be actuated by a tool.

Bone plates and bone screws are often used in orthopedic applications. For instance, bone plates and bone screws are used in connection with the stabilization or fusion of vertebral bodies in the spine, and are also used in connection with trauma applications, for instance, in fracture fixation. In many instances, there is concern that bone screws may loosen after implantation of a bone plate. To the extent that this occurs, it has been desirable to ensure that the screw does not fully remove itself from the bone and bone plate. Many plate systems include means for affirmatively locking the bone screw upon implantation through the plate. In other instances, a blocking mechanism is employed.

A blocking mechanism does not affirmatively hold the screw in its implanted position upon implantation or lock the bone screw to the plate; rather, it merely serves to block an already loosening screw from backing out any further from the plate.

Screw blocking mechanisms which are associated with the plate prior to insertion of a bone screw are known. In some instances, such blocking mechanisms allow for the insertion of the bone screw via the resiliency of the blocker itself. For example, a split ring may be housed in a recess in a bone screw receiving hall, such as that shown in U.S. Pat. No. 6,602,255.

It may be desirable to prevent expansion of a blocker after a bone screw and bone plate have been implanted. The present invention addresses this desirability.

SUMMARY OF THE INVENTION

The present invention may be practiced in one aspect by a bone plate having a top surface and a bottom surface with at least one screw hole therethrough, a blocker having an end and being movable by insertion of a bone screw into a blocking position such that the end is disposed over at least one bone screw hole and being movable by reason of the bone screw being inserted into the bone plate and bone during implantation, and a cam having an open orientation at which the blocker is permitted to move and a close orientation at which the blocker is substantially prevented from moving from the blocking position. The cam in this aspect of the present invention cannot be moved to the closed orientation unless the bone screw head is disposed distally of the blocker.

In accordance with another aspect of the present invention, the above bone plate is provided wherein the cam has a top surface and a bottom surface with a camming surface. The camming surface in the closed orientation may be arranged against the blocker. The camming surface may also, in open orientation, be arranged away from the blocker. In another aspect of the present invention, the blocker makes contact with the bone screw to lock the bone screw with respect to the plate upon implantation. In one aspect of the invention, the blocker is oriented above the bone screw, with no contact, such that it can only act as a blocker.

The above bone plate may also include a recess in which the blocker is positioned. The cam may include a boss disposed within an aperture, the boss being rotatably engaged within the aperture such that the cam may rotate from a closed orientation to an open orientation.

The blocking end of the blocker may be arcuate in shape such that it generally follows the arcuate shape of the bone screw hole. The arcuate shape of the blocking end may correspond to the arcuate shape of the bone screw hole, or may differ somewhat from the arcuate shape of the bone screw hole. In one aspect of the present invention, the blocker may extend over the periphery of bone screw hole by about 25% of the perimeter. In another aspect, it is about ⅓ of the periphery. Of course, as long as the blocker can be moved upon the insertion of the bone screw, the coverage on the perimeter of the bone screw hole may be larger.

In another aspect of the present invention, the bone plate is part of a system that includes at least a bone screw, or preferably a bone screw for each bone screw-receiving hole.

In connection with another aspect of the present invention, a method may be employed practicing the steps of providing a plate having a blocker which extends over a portion of a bone screw receiving hole in a bone plate, inserting a bone screw through the bone screw receiving hole, and simultaneously moving the blocker away from the screw hole to allow insertion of the bone screw, continuing insertion until the bone screw passes the blocker to allow the blocker to move back into the blocking position, and manipulating the cam from an open orientation to a closed orientation at which movement of the blocker from the blocking position is substantially prevented.

Yet a further aspect of the present invention may be practiced by a bone plate having a top surface and a lower surface and at least two bone screw receiving holes therethrough, undercuts in the periphery of at least a portion of the bone screw receiving holes, a blocker housed within the recess, the blocker having blocking ends which extend over portions of the respective bone screw receiving holes such that the blockers in a blocking position at which it is above a bone screw seated in the plate and in a bone during implantation and can block the bone screw from backing out of the bone plate should the bone screw loosen, the blocker being movable from the blocking position upon insertion of the respective bone screw, whereby the bone screw causes the blocker to move away from the bone screw receiving hole to allow insertion until the bone screw passes the blocker and the blockers thereby permitted to return to the blocking position. In connection with this aspect of the present invention, the blocker may be seated in a recess which is coextensive with the grooves around the least portion of the periphery of the bone screw receiving holes, and the recess in the plate may include a further groove opposition the bone screw receiving holes. The aspect of the present invention may also include a blocker fixing device which, after insertion of the bone screws in the bone plate and into bone, can be actuated by a surgeon to prevent the blocker from moving from the blocking position.

In another aspect of the present invention, a bone plate is provided, the bone plate having at least a pair of holes for receiving bone screws during implantation, a blocker associated with the plate and overlapping a portion of both the bone screw holes, a first blocker fixation element associated with a first bone screw hole and a second blocker fixation element associated with a second bone screw hole, the first and second blocker fixation elements being independently operable to selectively lock the blocker in a position overlapping the respective screw hole. In connection with the aspect of the present invention, the blocker fixation elements may be rotatable devices having camming surfaces to engage a cam receiving surface on separate portions of the blocker. Effectively, a surgeon would be required to move each blocker fixation element independently of the other blocker fixation elements after a bone screw has been inserted through the plate and into bone such that the blocker cannot be moved from the blocking position as set forth in connection with this or other previous aspects of the present invention.

In connection with another aspect of the present invention, a bone plate includes at least one bone plate receiving hole and a recess communicating with the bone screw receiving hole, the recess including a rotatable member that is movable between an open position at which a bone screw can be inserted into the bone screws receiving hole and a closed position at which the member overlays a portion of bone screw receiving hole to block a bone screw from further backing out should the bone screw begin to back out after implantation. The member may include an opening which engages, in the closed position, a protrusion in the recess of the plate to lock the member in the blocking position.

In connection with another aspect of the present invention, a block plate screw receiving hole, and a hinged member which is hingedably movable between an open position and at which a bone screw could be inserted into the bone screw hole and a close position at which the hinged member is in a blocking position to overlay a portion of the hole and block a bone screw from further backing out should the bone screw begin to back out of bone after implantation of the bone screw and the bone plate.

In connection with this aspect of the present invention, the hinged member may include a flexible portion which facilitates locking of the hinged member in the blocking position following movement from the open position and after a bone screw is inserted into the bone screw hole.

Another aspect of the present invention is similar to the foregoing except that the hinge member is hingedably connected to the plate in a central opening between sets of bone screw receiving holes. The hinged member would be closed to the blocking position after the bone screws have been implanted, and the hinge member would overlay a portion of at least two bone holes to block further backing out of the bone screws. The hinged member would have an opening to receive a projection extending from the plate between the holes to thereby lock the hinge member in the blocking position after the bone screw holes are implanted.

In connection with yet another embodiment of the present invention, a bone plate has at least two holes, a blocking member positioned between the two holes and being slideable along an axis of the plate such that an enlarged portion of the blocking member extends over the holes to block bone screws from further backing out after the bone screws have been implanted. The blocking member includes a slot in an arrow portion and is connected to the plate via the slot, there being a fixation member allowing the blocking member to slide relative to an axis of the plate until the enlarged portion of the member overlays the holes, at which time the fixation member can be utilized to lock the blocking member in the blocking position.

The present invention provides a plate system wherein the bone screw, if loosened after implantation, is blocked from loosening beyond the blocker (alternatively, called the spring bar). The present invention also provides a blocking system wherein the blocker operates without requiring further actuation beyond implanting the screw past the blocker. A secondary action of a cam is provided to ensure that the movement of the bone screw does not displace the blocker upon potential backout of the bone screw. The present invention further provides the surgeon with a tactile and visual feedback as to the position of the bone screw. The feedback may result from the loss of the force exerted by the blocker on the head of the screw when the screw is tightened past the blocker. The feedback may include an audible click when the screw moves past the blocker. The feedback may also result from visual observation of the position of the blocker. The blocker may be colored to enhance such visual feedback. The feedback also comes from the secondary action of manipulating a feedback device, i.e., the cam. The simple secondary action of manipulating the cam being, in and of itself, a feedback to the surgeon, even beyond any tactile feedback from the cam.

One aspect the invention provides a bone plate having a top surface and a bottom surface and at least one screw hole adapted to receive a bone screw. A flat is formed on the top surface of the bone plate, and at least a portion of the flat borders the screw hole. A blocker is provided, the blocker being adapted for insertion in the flat and having a screw end and a base end. At least a portion of the screw end is shaped to match the periphery of the screw hole and projects over the screw hole when the blocker is inserted in the flat. At least one leg is connected to the screw end and extends towards the base end. The leg is capable of elastic deflection. In use, when the screw is inserted in the screw hole, a portion of the bone screw comes in contact with the screw end, and as the screw advances into the bone plate, the blocker is deflected away to allow the screw head to move past the blocker, after which the blocker projects over the screw head. The blocker may be colored. A cam may be rotated to secure the blocker in its blocking position.

BRIEF DESCRIPTION OF THE DRAWINGS

FIG. 13 is a perspective view of a bone plate system in accordance with a further embodiment of the present invention.

FIG. 14 is another perspective view of one end of the bone plate as shown in FIG. 13.

FIG. 15 is a further perspective view of one end of the bone plate as shown in FIG. 13.

FIG. 24 is a perspective view of the bone plate system of FIG. 22 in a substantially open position.

FIG. 25 is a perspective view of the bone plate system of FIG. 22 in a substantially closed position.

FIG. 30 is a perspective view of a two-level bone plate system in accordance with still another embodiment of the present invention.

DETAILED DESCRIPTION

Figure 1:
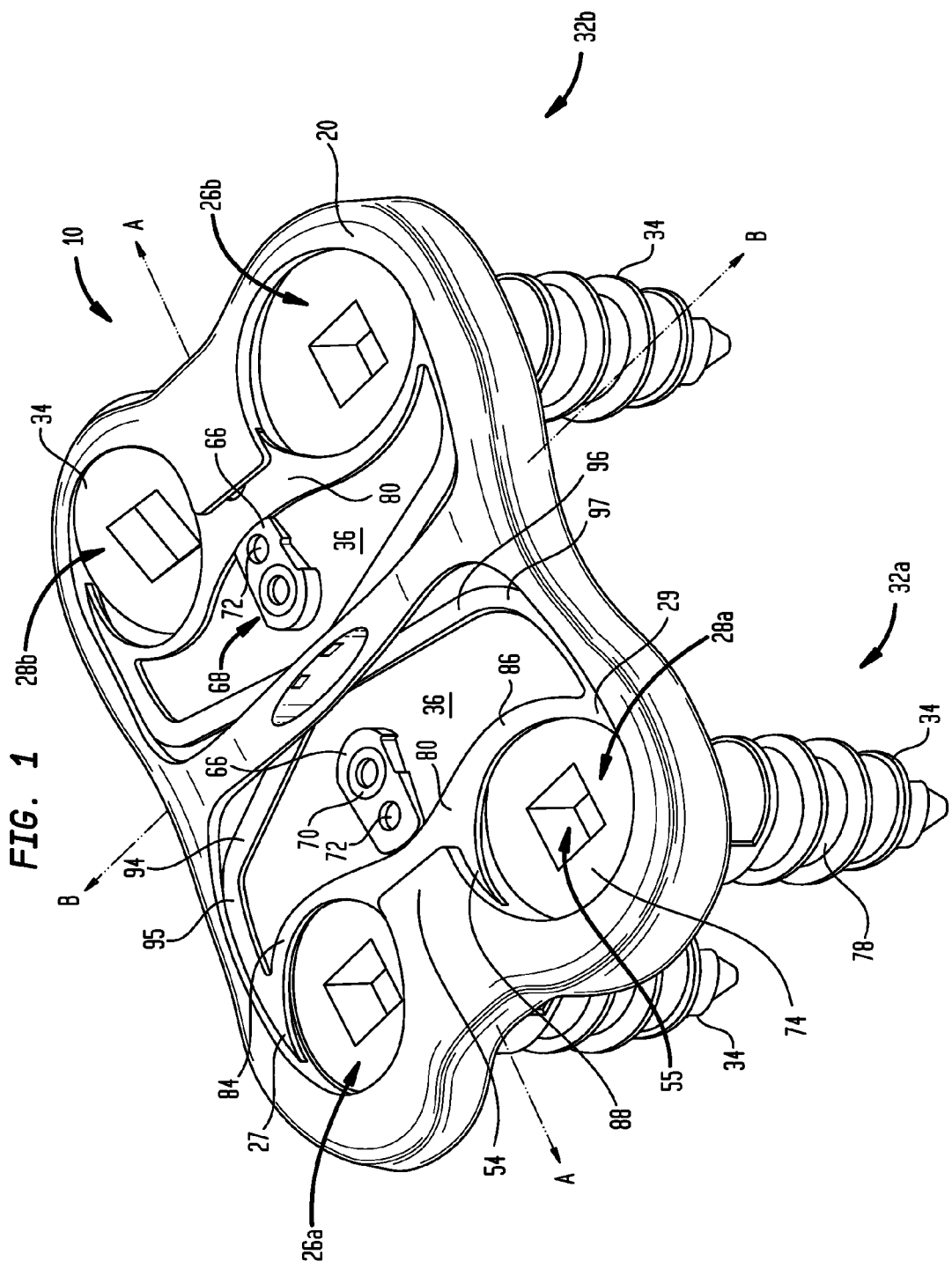
FIG. 1 is a perspective view of a one-level bone plate system in accordance with an embodiment of the present invention.

In accordance with an embodiment of the present invention, FIG. 1 depicts a one-level bone plate system 10 that may be used to stabilize or fuse vertebral bodies in the cervical or other region of the spine. System 10 is comprised of a bone plate 20, two screws 34, and blockers 80. In a more preferred embodiment, the system also includes a blocker fixation element, which may take the form of a cam 66, and a pin 70. Bone plate 20 includes a first pair 32a of screw holes 26a and 28a designed to receive bone screws 34, and likewise a second pair 32b of screw holes 26b and 28b.

It is to be understood that reference numerals pertaining to any one component are also descriptive of additional identical components of system 10, though such numerals may be omitted from the figures for clarity and ease of review. Furthermore, insofar as alternate embodiments are described, it is contemplated that a system may instead include more than one embodiment of a certain component.

Bone plate 20 includes a bottom side 24 and a top side 22, and may be shaped to mount across two vertebrae. Bone plate 20 may possess a first curvature along an axis A in its longitudinal plane that allows bone plate 20 to follow the natural lordosis of the section of spine for which bone plate 20 is intended. In addition, bone plate 20 may have a second curvature along an axis B in its transverse plane that allows bone plate 20 accommodate or to match as closely as possible the shape of the body of the vertebra or vertebrae to which it is connected. It is to be understood that the opposing ends of bone plate 20 are mirror images of one another, with first pair 32a being located opposite second pair 32b. Bone plate 20 further includes a flat 36 adjacent top side 22 and having a plate hole 98 for accepting pin 70.

Figure 2:
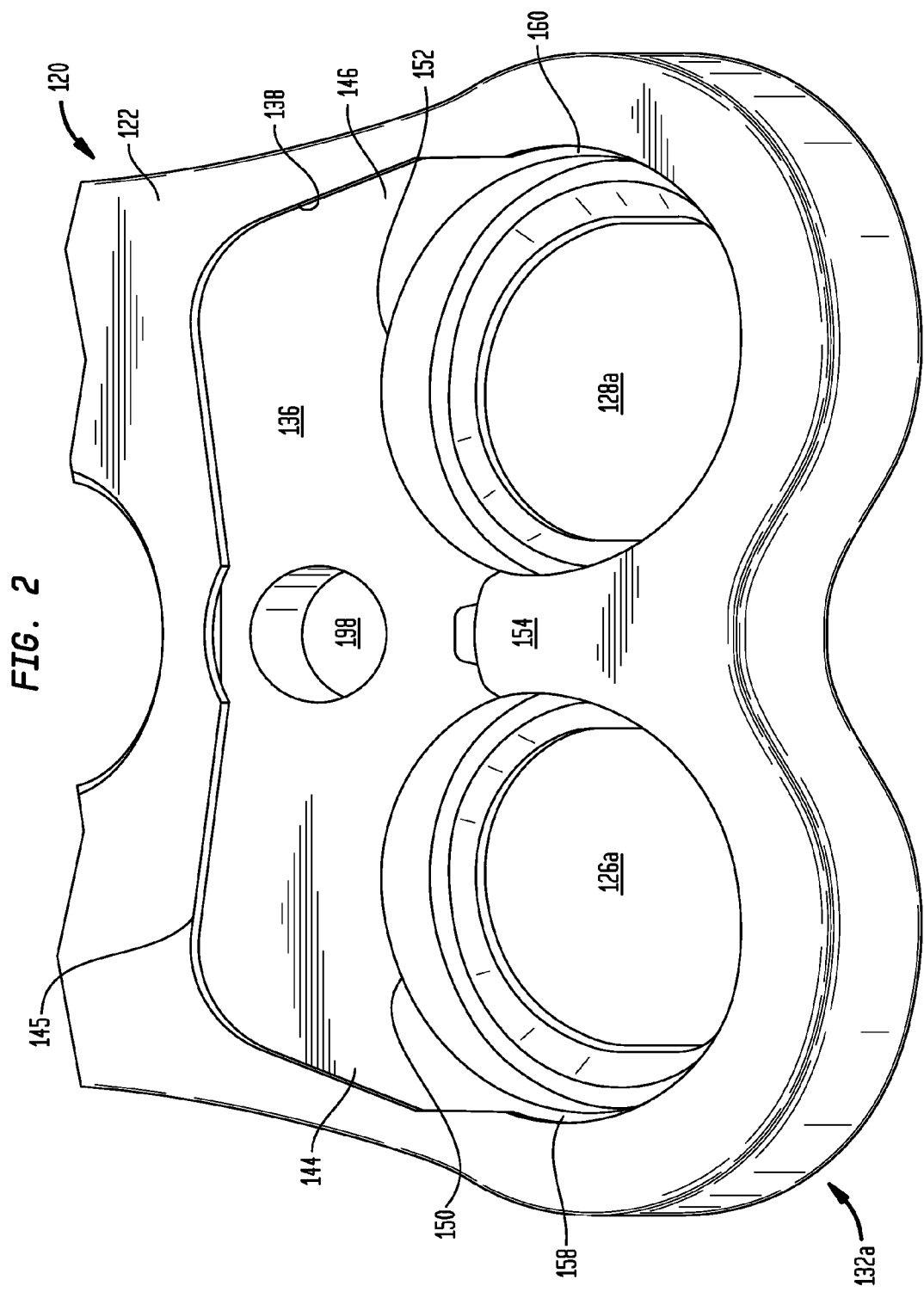
FIG. 2 is a perspective view of an end of a bone plate in accordance with another embodiment of the present invention, the other end of the bone plate being a mirror image thereof.
Figure 3:
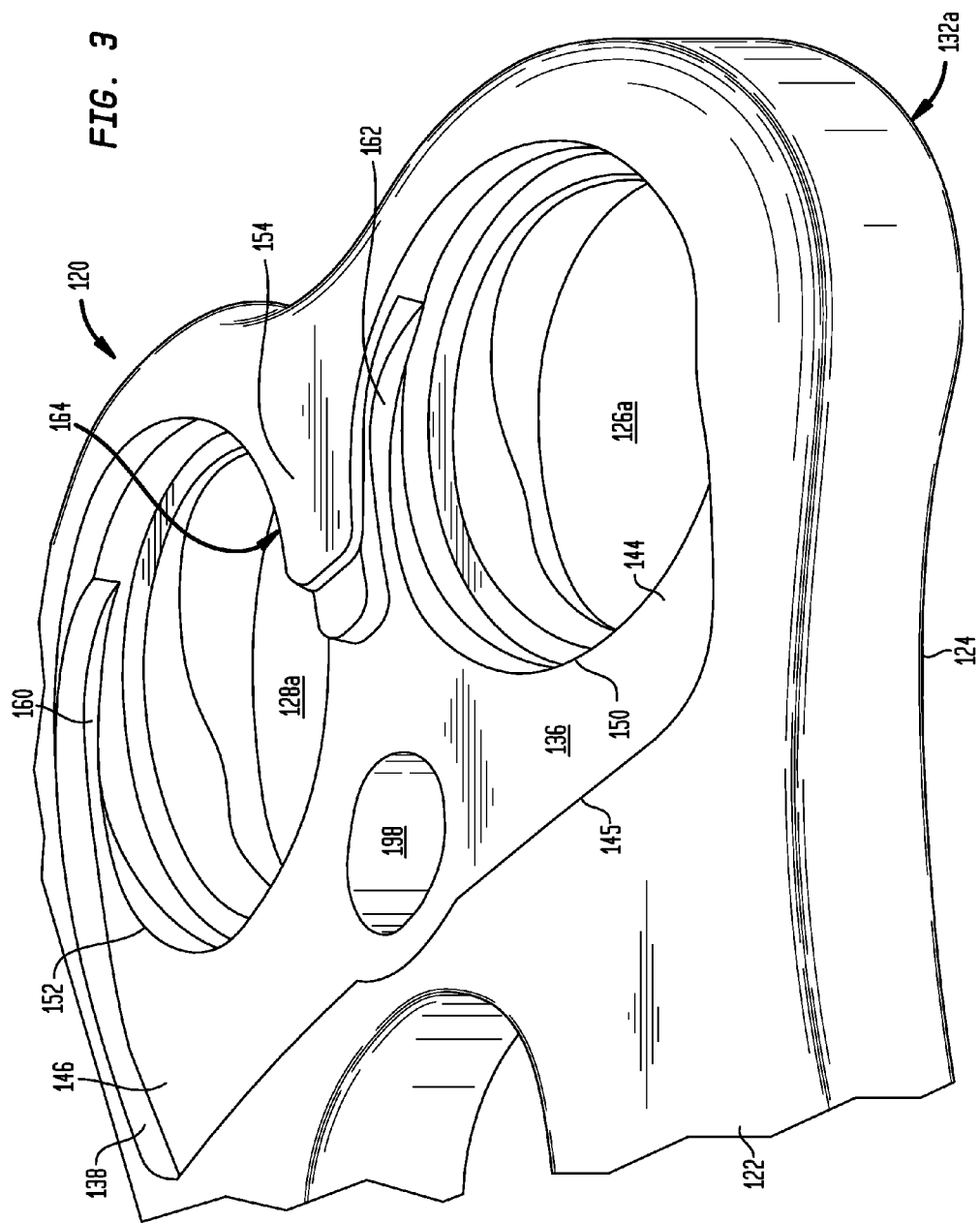
FIG. 3 is another perspective view of the end of the bone plate as shown in FIG. 2.

In another embodiment similar to FIG. 1, shown in FIGS. 2 and 3, one end of bone plate 120 having flat 136 and pair 132a is more clearly depicted, with the other end being a mirror image thereof. Flat 136 includes a first side 144, a second side 146, and a rear side 145. A wall 138 substantially surrounds flat 136 at its periphery, and may provide an undercut in the form of an angle therewith of less than 90 degrees. As such, wall 136 may project over flat 136. Alternatively, wall 138 may form the undercut by being stepped and having an upper portion extending over flat 136. The purpose of the undercut is to provide a structure on bone plate 120 to mate with and contain blocker 80. Flat includes first and second arcuate portions 150 and 152 that coincide with the periphery of screw holes 126a and 128a, respectively. Flat 136 further includes a projection 148 being disposed between screw holes 126a and 128a, and a cantilever 154 extending over projection 148. Cantilever 154 is coplanar with top side 122. Flat 136 includes first and second sides 144 and 146 which form first and second front ends 158 and 160, respectively, being adjacent to portions of the periphery of screw holes 126s and 128a, respectively. Bone plate 120 includes first and second recesses 162 and 164, each being disposed opposite screw hole 126a and 128a, respectively, from first and second front ends 158 and 160, respectively. As shown in FIG. 3, first recess 162 is disposed between flat 136 and cantilever 154, and extends between screw hole 126a and projection 148. Likewise, second recess 164 is similarly disposed between flat 136 and cantilever 154, and extends between screw hole 128a and projection 148.

Cam 66 is depicted in FIG. 1, is mounted on flat 36, and includes a first cam opening 68 and a second cam opening 72. Pin 70 passes through first cam opening 68 and plate hole 98. Ends of pin 70 may preferably be flared to rotatably secure cam 66 to bone plate 20 such that cam 66 may rotate about pin 70. Second cam opening 72 is designed to receive a driver in order to rotate cam 66. Both cams 66 depicted in FIG. 1 are shown in an closed position which is defined as the orientation wherein both first cam opening 68 and second cam opening 72 are aligned parallel to axis A. Alternatively, an open position of cam 66 is defined as the orientation wherein both first cam opening 68 and second cam opening 72 are aligned parallel to axis B. Cam 66 may be moved between open and closed positions by engaging a driver with second cam opening 72 to rotate cam 66 about pin 70.

Figure 4:
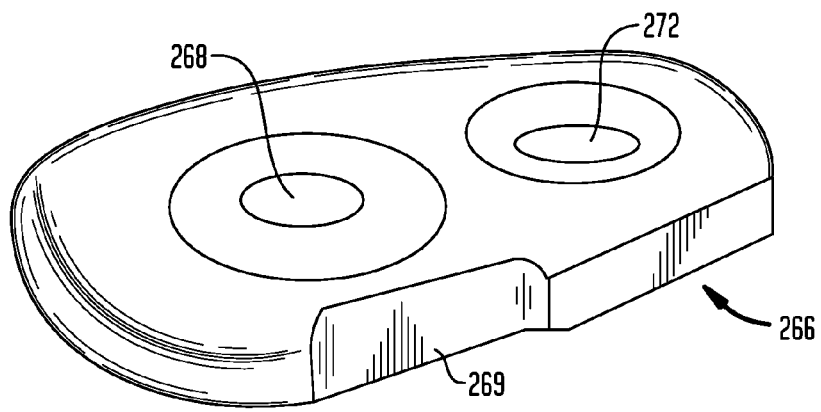
FIG. 4 is a perspective view of a cam in accordance with an embodiment of the present invention.

According to another embodiment, cam 266 is depicted in FIG. 4. Cam 266 includes a first notch 269 and a second notch 271 (not shown) disposed on opposite sides thereof. First notch and second notch 271 provide a gripping tool an alternate means in order to grasp and rotate cam 266 between open and closed positions.

As depicted in FIG. 1, blocker 80 is inserted into flat 36 and is constructed to act as a spring mechanism with respect to flat 36. Blocker 80 includes first and second arcuate regions 84 and 86 adjacent to and shaped to correspond with screw holes 26a and 28a, respectively. First and second outer edges 27 and 29 of blocker 80 are designed to slide along front ends 58 and 60, respectively, of flat 36. Arcuate regions 84 and 86 converge to form a central region 88 which is disposed, at least in part, below cantilever 54. Blocker further includes first and second legs 94 and 96 having respective first and second bent portions 95 and 97. Bent portions 95, 97 are flexibly bent at approximately a 90 degree angle, and preferably at an angle that is slightly greater than 90 degrees.

Blocker 80 is designed with respect to flat 36 such that the portions of first and second legs 94 and 96 disposed closest to cam 66 are pressed against wall 38. First and second legs 94 and 96 are biased such that in a resting position, arcuate regions 84 and 86 are disposed to overlap screw holes 26a and 28a, respectively, and corresponding arcuate portions 50 and 52, respectively. When force is exerted on blocker 80 via either or both of arcuate regions 84 and 86, blocker 80 is pushed away from screw holes 26a and 28a causing first and second legs 94 and 96 to bend. First and second legs 94 and 96 may be replaced by any suitable structure that would allow blocker 80 to move away from and automatically spring back toward screw holes 26a and 28a upon application of a force to blocker 80 and subsequent removal of the force, respectively. Such a force is typically provided by one or more screws 34 as same are inserted through screw holes 26a and/or 26b.

Blocker 80 may be provided in any suitable color, although preferably a different color than any other component of system 10, in order to differentiate therefrom and to provide visual feedback to the surgeon. Blocker 80 may be comprised of a polymeric material, in which case color can be added to the material during manufacture, or alternatively after manufacture by paint or the like. Blocker 80 may alternatively be comprised of a rigid biocompatible material, such as metal, wherein the color may be added via an anodization process.

Bone screw 34 may either be a fixed-angle or a variable-angle screw. A variable-angle bone screw 34 may be inserted at an angle to a central axis of any of screw holes 26a, 28a, etc. Bone screw 34 includes a threaded shank 78 and a head 74 having a shoulder 76 (not shown). Head 74 has a screw head recess 55 that is sized to be engageable by an insertion tool, described below. Screw head recess 55 is depicted as being substantially cubic, which is preferable as an associated driving tool is able to better grip bone screw 34 and provide greater torque. Of course, bone screw 34 could be adapted such that head 74 is engageable with a standard driving tool, such as a flat-head or Phillips-head screw driver.

Figure 8:
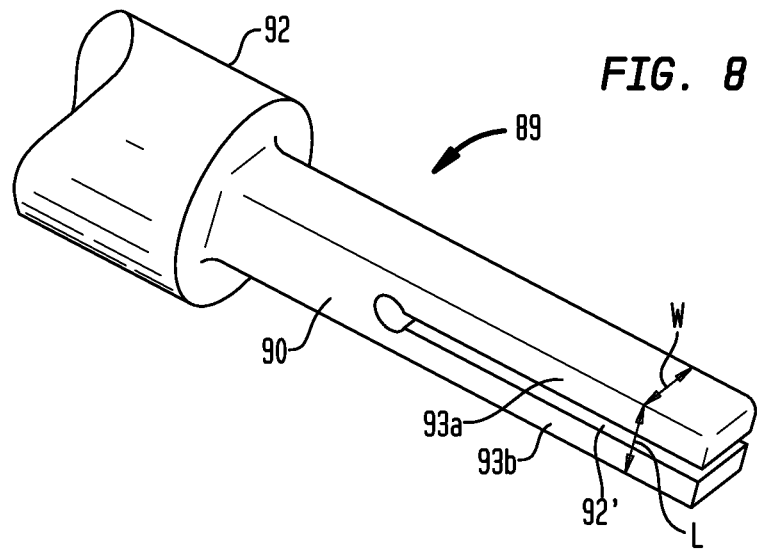
FIG. 8 is a perspective view of an end of a tool in accordance with an embodiment of the present invention.
Figure 9:
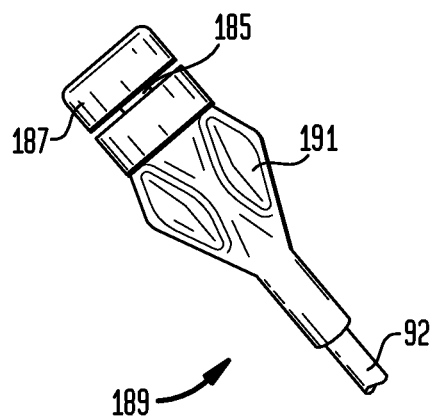
FIG. 9 is a plan view of a handle of the tool in accordance with another embodiment of the present invention.
Figure 10:
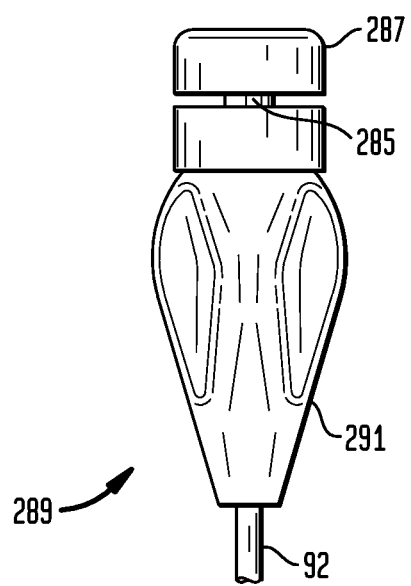
FIG. 10 is a plan view of a handle of the tool in accordance with a further embodiment of the present invention.
Figure 11:
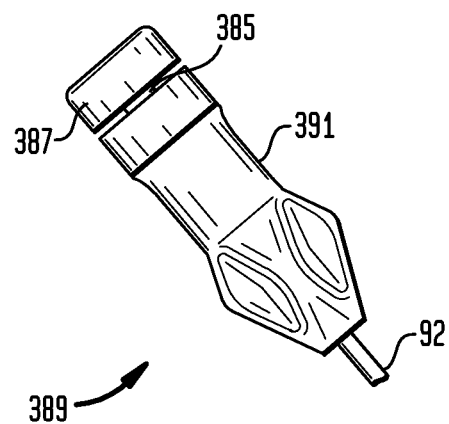
FIG. 11 is a plan view of a handle of the tool in accordance with still another embodiment of the present invention.
Figure 12:
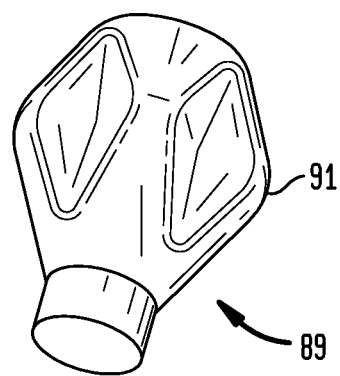
FIG. 12 is a plan view of a handle of the tool in accordance with another embodiment of the present invention.

According to another embodiment, FIG. 8 shows an end 90 of a tool 89 utilized, for example, for inserting bone screw 34. End 90 has a cross-section in the shape of a quadrilateral, more specifically a rectangle or square. The cross-section of end 90 substantially corresponds with the shape of screw head recess 55, as shown in FIG. 1. While end 90 and screw head recess 55 are shown to be substantially square, other non-circular orientations are contemplated, such as a triangle, pentagon, hexagon, star, etc. The substantially square cross-section of end 90 is preferable as it allows for a secure connection with bone screw 34 while transmitting a great amount of torque without stripping the interior of screw head recess 55. End 90 includes a width W that is no larger than one dimension of screw head recess 55. End 90 also includes a length L that may be made slightly larger then another dimension of screw head recess 55. End 90 may further include a slit 92' which separates end 90 into a first end piece 93a and a second end piece 93b. Such a construction allows end pieces 93a and 93b to be pressed towards one another during insertion of end 90 into screw head recess 55, thereby causing end 90 to exert an outward force on the interior of screw head recess 55 to removably secure screw 34 to end 90.

FIGS. 9-12 show various embodiments of a handle 91, 191, 291, 391 included on a tool 89, 189, 289, 389, respectively, in accordance with additional embodiments of the present invention. Handles 91, 191, 291, 391 are shaped differently to provide the surgeon with different configurations for comfort and driving purposes. End 90 may be common to each embodiment of tool 89, 189, 289, 389, with handle 91, 191, 291, 391 connected to end 90 via a shaft 92. Tools 189, 289, and 389 each include a pommel 187, 287, and 387 and a pommel rod 185, 285, and 385, respectively. Pommel 187 and pommel rod 185 are rigidly connected, and pommel rod 185 is disposed within handle 189 such that pommel 187 and handle 189 may each pivot independently about an axis through pommel rod 185. Such a configuration is preferable as it allows for pressure to be applied to pommel 187 in a distal direction while allowing handle 189 to be pivoted about an axis through pommel rod 185. This provides the ability to more securely anchor bone screw 34.

The assembly of system 10 can be seen in FIG. 1. Blocker 80 is inserted into flat 36 such that the outermost portions of blocker 80 in its rested state contact wall 38 and are contained by the undercut formed between wall 38 and flat 36. Outer edges 27 and 29 of arcuate regions 84 and 86 are disposed in recesses 62 and 64. Cam 66 is depicted in its closed position where it pushes against blocker 80 and arcuate regions 84 and 86 are projected over screw holes 26a and 28a, respectively. Blocker 80 is substantially laterally blocked in this position.

In use, bone plate 20, with cam 66 in open position, is placed over vertebrae. Next, screws 34 are advanced one at a time through bone plate 20 and into the bone of the respective vertebra using tool 89. As screw 34 is advanced through bone plate 20, the head portion of screw 34 pushes against the corresponding arcuate region 84, 86 of blocker 80, thereby pushing blocker 80 away from screw holes 26a and 28a. Blocker 80 may exert a spring force toward screw holes 26a and 28a in the range of about one pound, though alternative configurations may provide blockers that exert higher or lower forces. A second driver adapted for final tightening may be used to finally tighten screw 34. Once screws 34 are properly inserted through bone plate 20, cam 66 is rotated to its closed position in order to secure blocker 80 with respect to screw holes 26a and 28a.

The force provided by blocker 80 provides the surgeon with a tactile feedback when inserting screw 34 that will alert the surgeon as to when screw 34 has moved distally of blocker 80. Such feedback may include an audible clicking sound as screw 34 moves past blocker 80. The feedback may also be visual, the result of the surgeon observing the position of the blocker relative to screw 34. As mentioned above, blocker 80 may also be colored to enhance visual feedback. If screw 34 has not been fully inserted, and therefore has not traveled past the edge of arcuate region 84, blocker 80 will not close. Further feedback is provided to the surgeon in that the cam cannot be moved into its closed position until and unless the screw head has been fully inserted, i.e. the screw head is disposed distally of the blocker.

The above procedure may then be repeated for additional screws 34. The result is that blocker 80 may be disposed proximal to screws 34, though not necessarily touching same. As may occur after surgery, one or more screws 34 may loosen and tend to back out of the bone into which they are inserted. Any loosening of screws 34 would result same coming into contact with blocker 80, thereby preventing screws 34 from further backing out. This is repeated for each pair of screws. It would be clear to one skilled in the art that the method of use of bone plates of different size is similar and does not vary in any significant manner due to the size of the plate.

Figure 5:
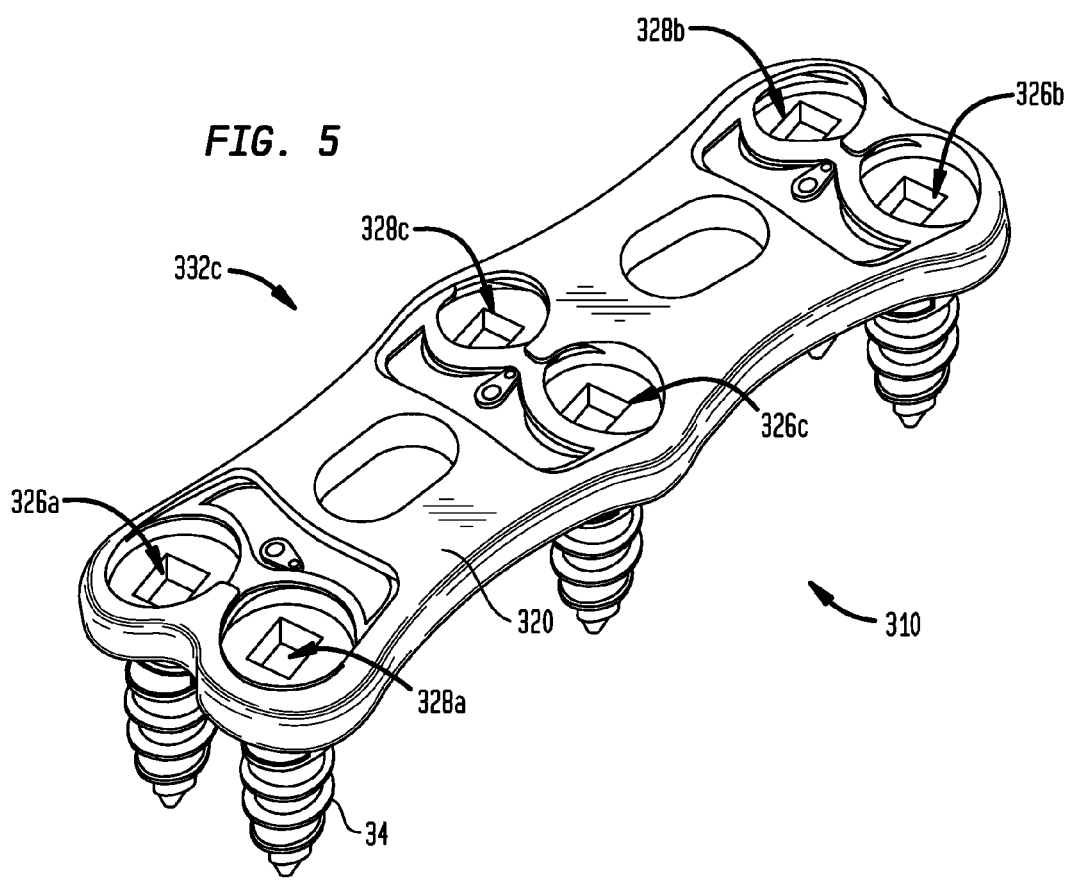
FIG. 5 is a perspective view of a two-level bone plate system in accordance with an embodiment of the present invention.

In accordance with another embodiment of the present invention, FIG. 5 depicts a two-level bone plate system 310 being comprised of a bone plate 320 and three blockers. Bone plate 320 is similar in construction to bone plate 20 except that it is longer and may cover three vertebrae. In the middle portion of plate 320, blockers are seen with a third pair 332c of screw holes 326c and 328c. Of course, blocker 380c and third pair 332c are as described above, though included at a middle portion of plate 320 as opposed to at an end thereof.

Figure 6:
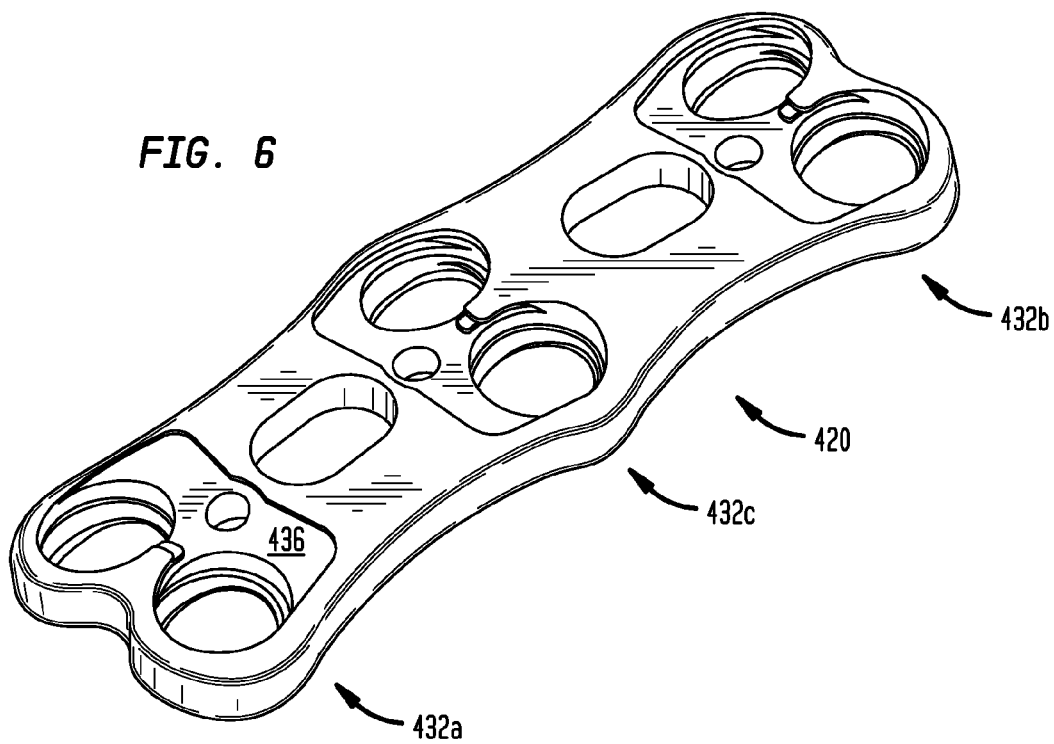
FIG. 6 is a perspective view of a bone plate in accordance with another embodiment of the present invention.
Figure 7:
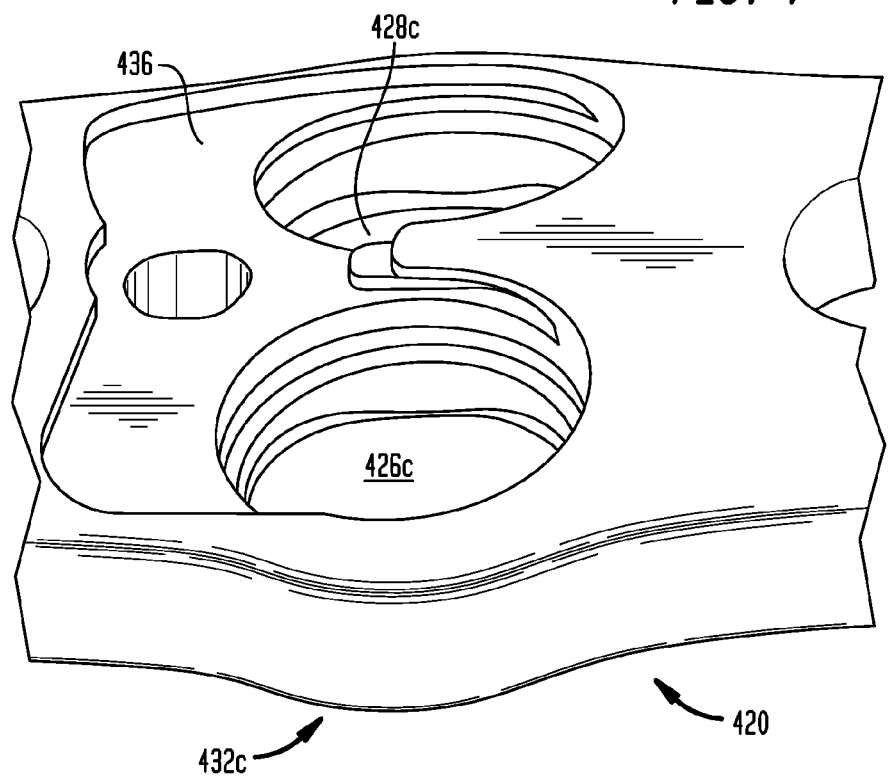
FIG. 7 is another perspective view of a central portion of the bone plate as shown in FIG. 6.

In another embodiment similar to FIG. 5, shown in FIGS. 6 and 7, a bone plate 420 and a middle thereof, respectively, are shown. By virtue of bone plate 420 being adapted for use across three vertebrae, it includes a third pair 432c of screw holes 426c and 428c. A three-level plate, a four-level plate, a five-level plate, et cetera will have additional pairs of screw holes for each additional level and an additional blocker associated therewith.

FIGS. 13-15 depict an additional embodiment of a two-level bone plate system 510 having bone plate 520 and two blockers 580. It is noted that each of FIGS. 13-15 depict one end of bone plate 520 with the opposite end being a mirror image thereof. As well, any level of bone plate may be created using this particular configuration, as is discussed above. Bone plate 520 includes central portion 548 being substantially as wide as cantilever 554. Central region 588 of blocker 580 is disposed beneath cantilever 554 at least in its blocking position. Bone plate 580 further includes posts 540 and 541 adjacent screw holes 526a and 528a, respectively, for rotatably connecting cams 566 to body 580, preferably through a snap fit. Blocker 580 includes two notches 581 and 582 which each correspond with a wing 583 of cam 566. In a blocking position, blocker 580 is disposed to overlap screw holes 526a and 528a wherein one or both cams 566 are oriented such that wing 583 is engaged with notch 581 and/or 582. Cams 566 may be rotated by a tool, as described above.

Figure 16:
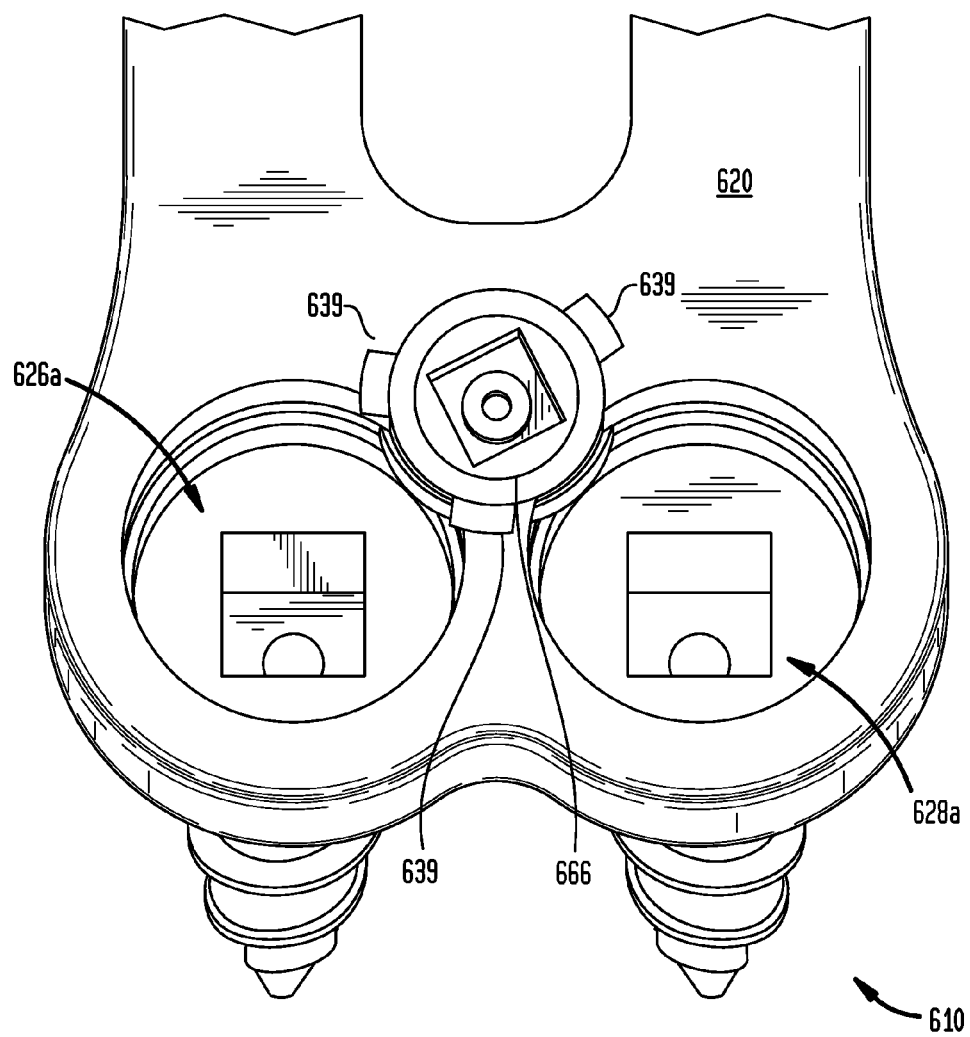
FIG. 16 is a perspective view of a bone plate system in accordance with still a further embodiment of the present invention.

FIG. 16 depicts another embodiment as bone plate system 610 including a cam 666 having three cam extensions 639. Cam 666 is rotatably connected to bone plate 620 such that when rotated into a locking position, at least one cam extension 639 overlaps with each of screw holes 626a and 628a, thereby preventing screws 34 from backing out.

Figure 17:
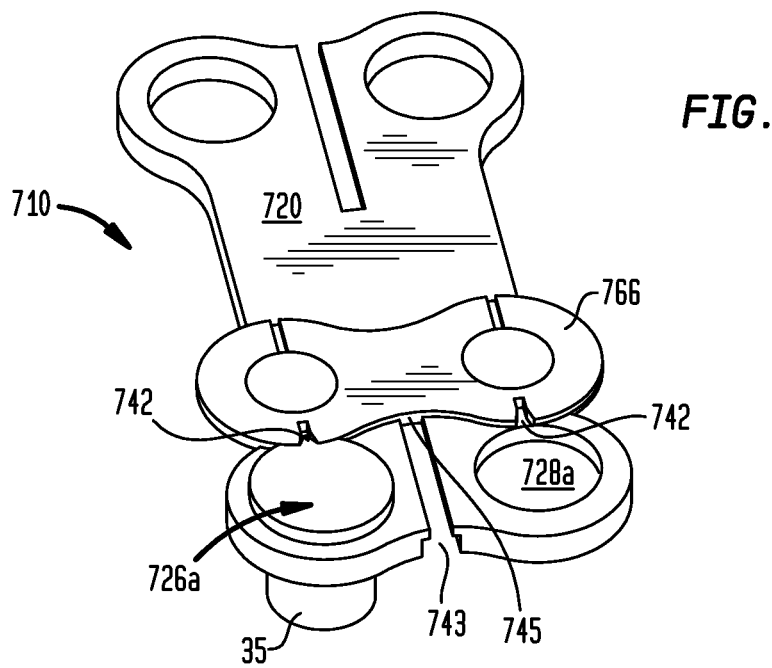
FIG. 17 is a perspective view of a bone plate system in a substantially open position in accordance with another embodiment of the present invention.
Figure 18:
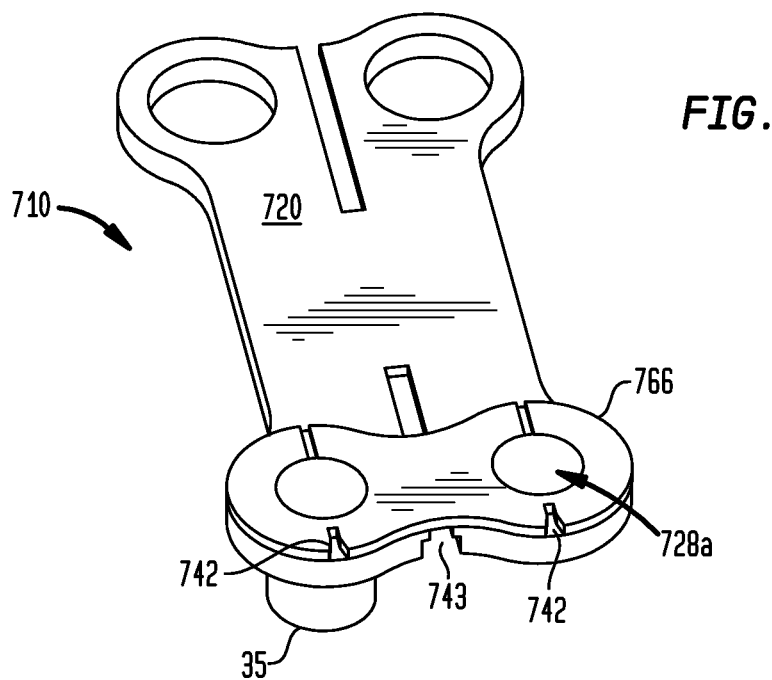
FIG. 18 is a perspective view of the bone plate system of FIG. 17 in a substantially closed position.
Figure 19:
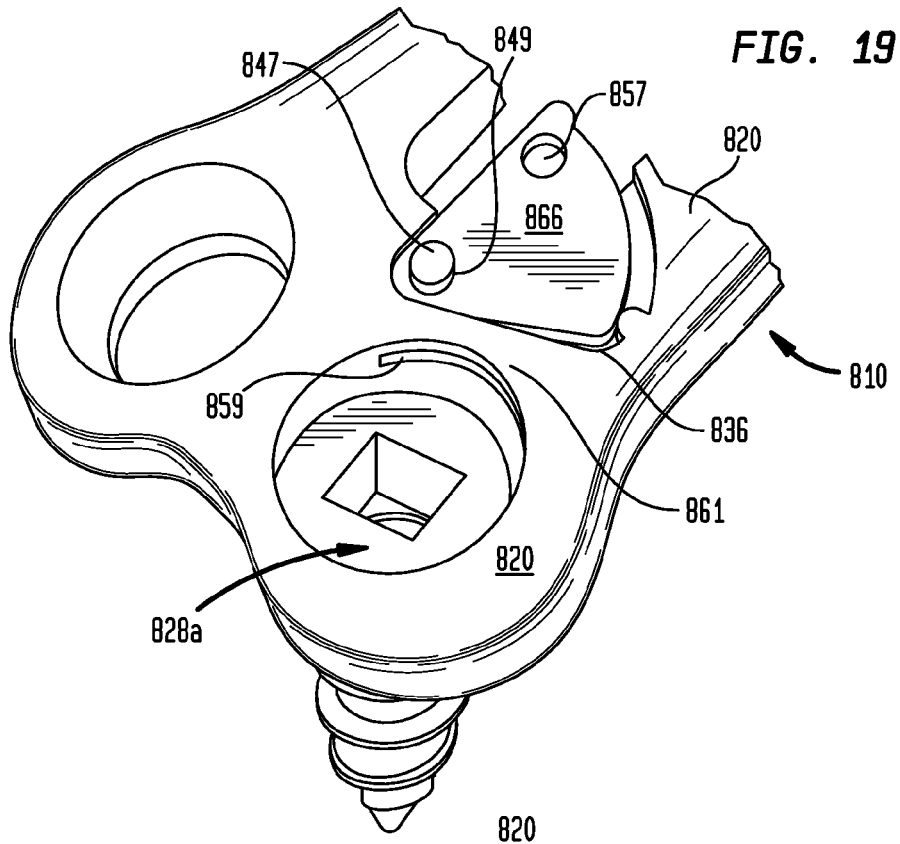
FIG. 19 is a perspective view of a bone plate system in a substantially open position in accordance with yet another embodiment of the present invention.

FIGS. 17 and 18 depict a substantially open position and a substantially closed position of a further embodiment as a one-level bone plate system 710. Cam 766 is disposed to substantially cover both screw holes 726a and 728a. Cam 766 includes a slide 745 which mates with a groove 743 in bone plate 720, which allows cam 766 to move between the substantially open position (as shown in FIG. 18), and the substantially closed position (as shown in FIG. 19). Cam 766 includes a break 742 which allows portions of cam 766 to move with respect to one another as cam 766 contacts and moves over screw 34 or, alternatively, a peg 35 as shown in FIGS. 17 and 18.

Figure 20:
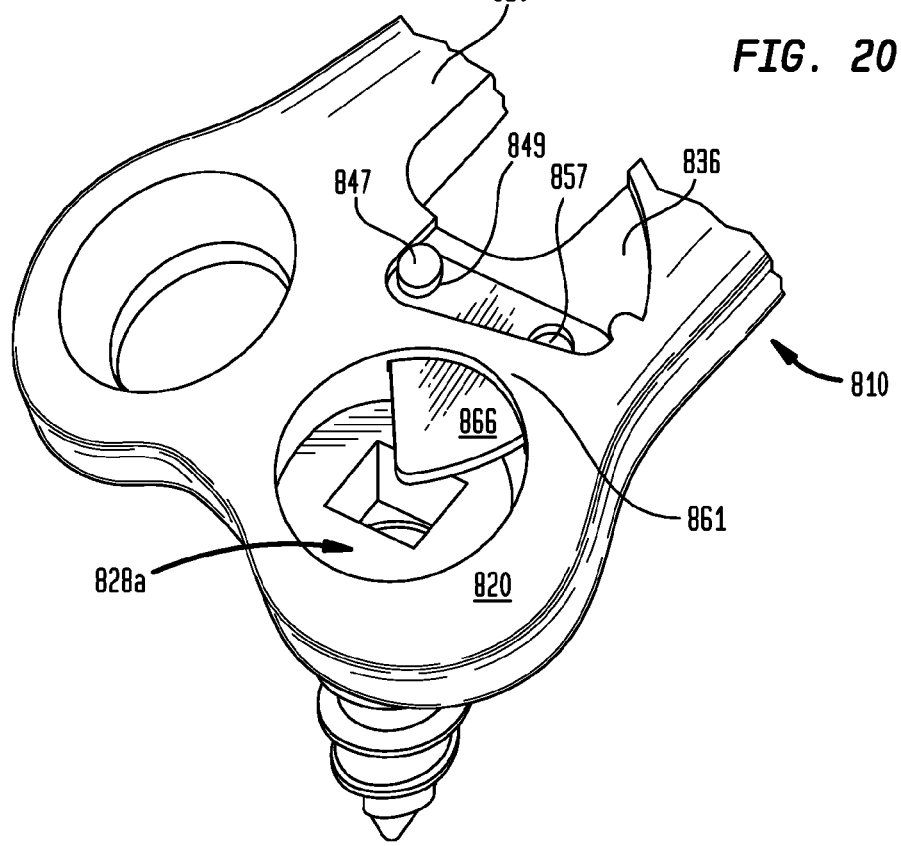
FIG. 20 is a perspective view of the bone plate system of FIG. 19 in a substantially closed position.
Figure 21:
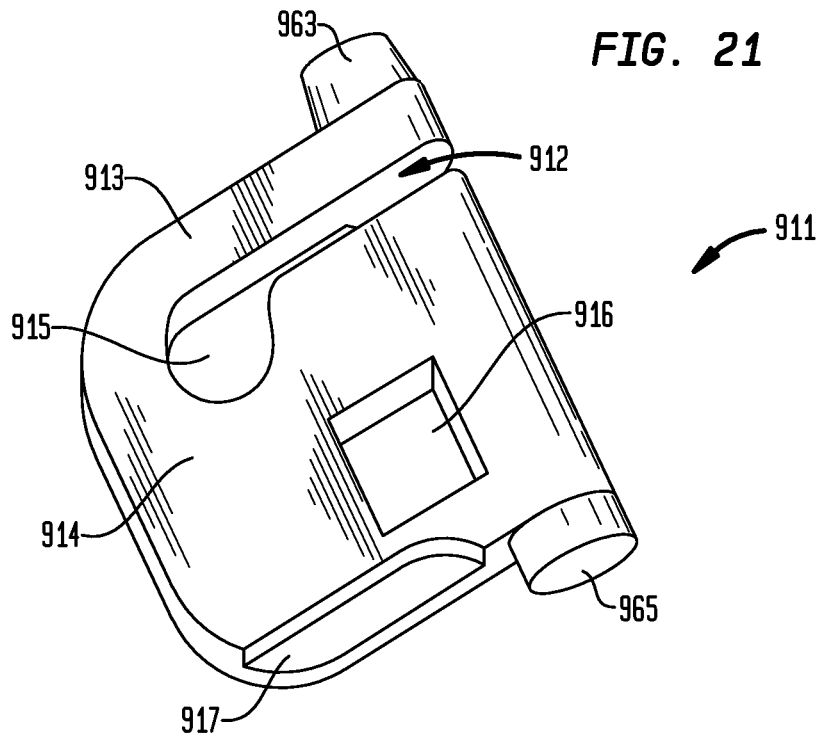
FIG. 21 is a perspective view of a cover according to still another embodiment of the present invention

FIGS. 19 and 20 depict bone plate system 810 in accordance with another embodiment. Bone plate 820 includes a knob 847 that engages with a primary cam hole 849 of cam 866, which takes on a triangular or pie-shaped orientation. Cam 866 is pivotable about knob 847. A bridge 861 extends over flat 836 between knob 847 and screw hole 828a, thereby forming a slot 859. Cam 866 is able to pivot through slot 859 in order to move into a closed position whereby a portion of cam 866 is disposed inside screw hole 828a and proximal of an inserted bone screw 34. Cam 866 further includes a secondary cam hole 857 which is configured to either receive a manipulation tool and/or to engage a secondary knob which extends from the plate in the recessed area in order to removably secure cam 866 in its closed configuration.

FIGS. 21-25 depict another embodiment of a bone plate system 910. Bone plate 920 includes first and second flats 936a and 936b adjacent screw holes 928a and 926a, respectively. A cover 911 includes a flap-like configuration, and anchors into flat 936a via cam ends 963 and 965. Thus, cover 911 may pivot about an axis through cam ends 963 and 965 when attached to bone plate 920. Cover includes a cover slot 912 separating a cover leg 913 from a cover body 914. Cover slot 912 includes a wide end 915 so as to prevent splitting or cracking of cover 911 as cover leg 913 is flexed toward and away from cover body 914 during insertion thereof into bone plate 920. Cover body 914 has a window 916 which may aid a tool in manipulating cover 911. Further, cover 911 includes a cover tab 917 on cover body 914 for mating with a plate tab 918 on bone plate 920. Of course, cover tab 917 could alternatively be placed on cover leg 913.

Figure 22:
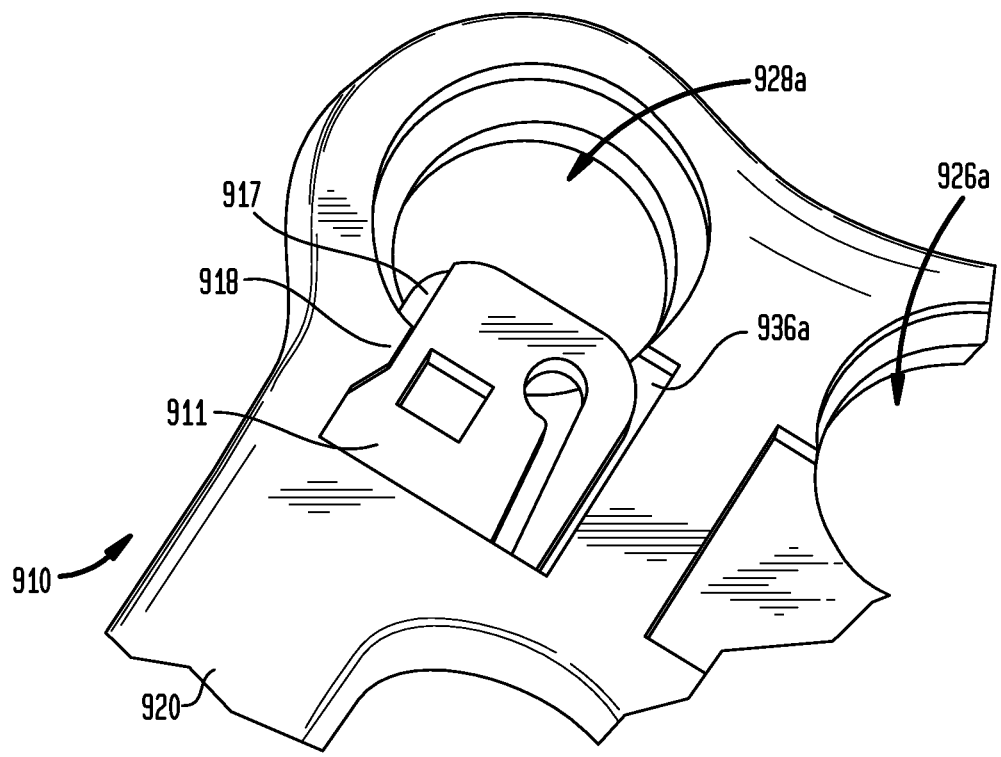
FIG. 22 is a perspective view of a bone plate system having including cover of FIG. 21.
Figure 23:
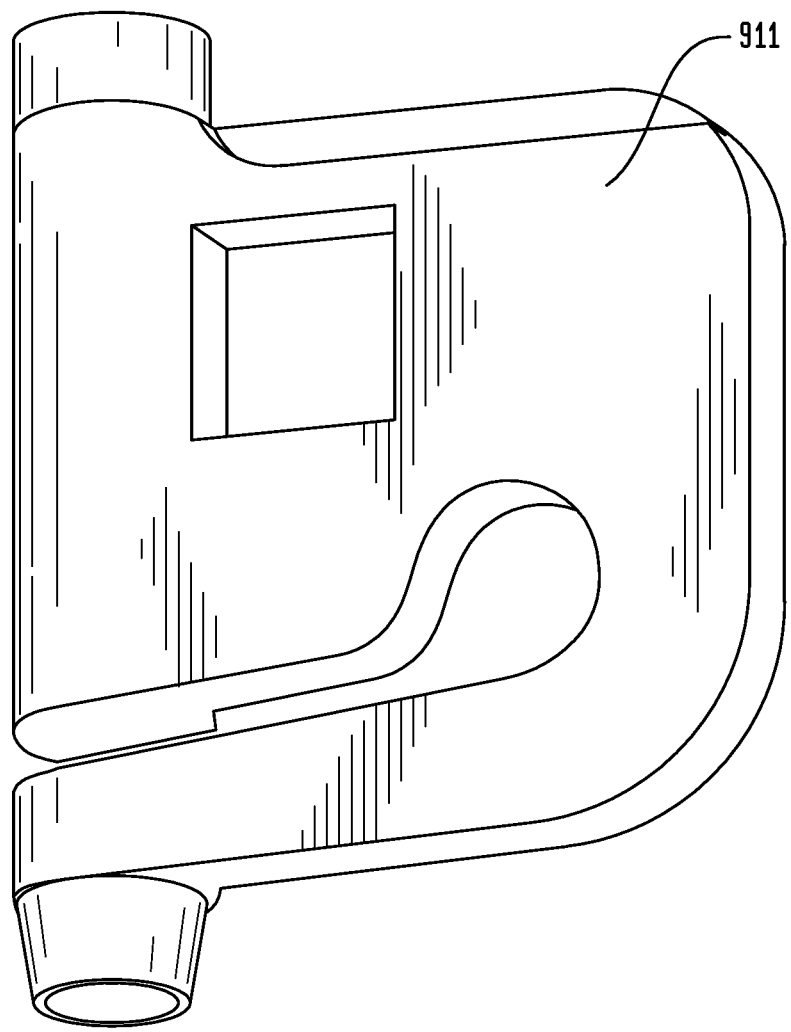
FIG. 23 is another perspective view of the cover of FIG. 21.

FIGS. 22 and 25 depict bone plate system 910 in a closed position with respect to cover 911 and flat 936a. Cover tab 917 is disposed distally of plate tab 918, providing a removably securable fit between same. In such a closed position, a screw 34 disposed in screw hole 928a is prevented from backing out, although it is not necessary or required for cover 911 to contact screw 34 to prevent such backout. FIG. 24 depicts bone plate system 910 in an open position with respect to cover 911. To open cover 911 from its closed position, a tool is used to provide a lifting force to cover 911 via window 916, wherein cover 911 yields and moves around plate tab 918. Alternatively, the lifting force may be applied to the non-anchored end of cover 911.

Of course bone plate system 910 may include a cover/flat configuration for each bone hole. It is noted that the cover provided for plate hole 926a would be a mirror image of cover 911 as depicted in the figures.

Figure 26:
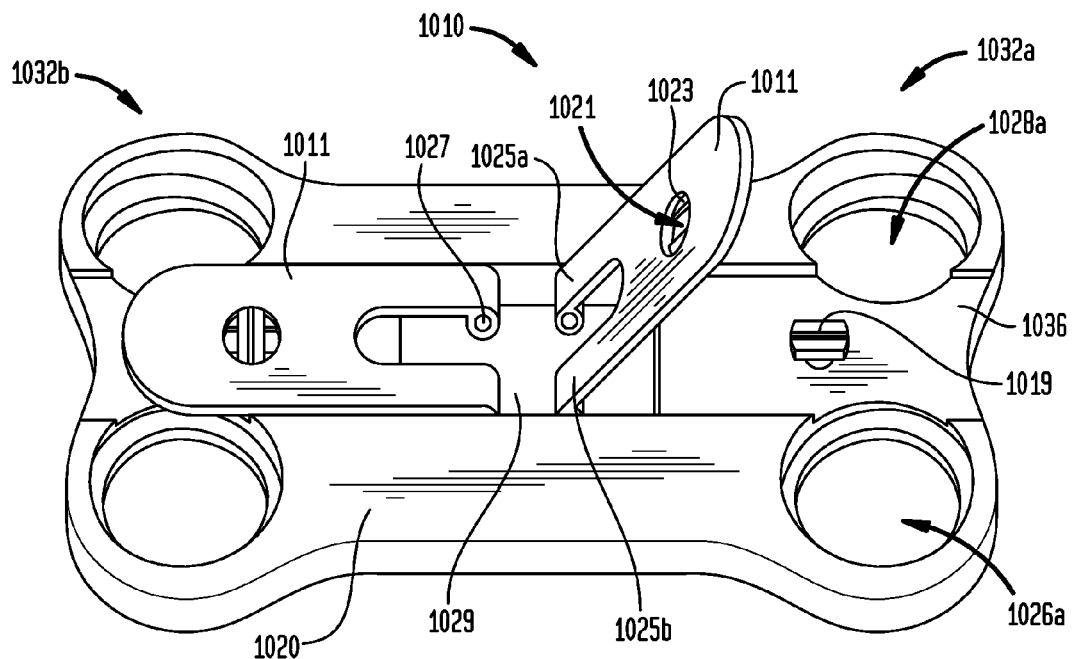
FIG. 26 is a perspective view of a bone plate system in accordance with yet another embodiment of the present invention.

FIG. 26 depicts another embodiment as a bone plate system 1010 having bone plate 1020 and two covers 1011. Each cover 1011 is disposed to overlap with a pair 1032a of bone holes 1026a and 1028a. Flat 1036 has a rotatable button 1019 which mates with a cover hole 1021 having at least one cover hole lip 1023. When cover 1011 is disposed against flat 1036 of bone plate 1020, cover hole 1021 seats around rotatable button 1019, which may then be rotated with respect to the axis of cover hole 1021 to engage the at least one cover hole lip 1023. In such a configuration, cover 1011 is in a substantially closed position with respect to bone plate 1020. Rotatable button 1019 may include any type of tool engaging distal end in order to receive a tool for rotation. For example, a standard Philips-head or flat end screwdriver may be used, or any other tool disclosed herein may be used.

Cover 1011 further includes cover legs 1025a and 1025b which connect with pins 1027 of bone plate 1020 so that cover 1011 may pivot with respect to bone plate 1020. Pins 1027 are disposed within a central opening 1029 of bone plate 1020.

Figure 27:
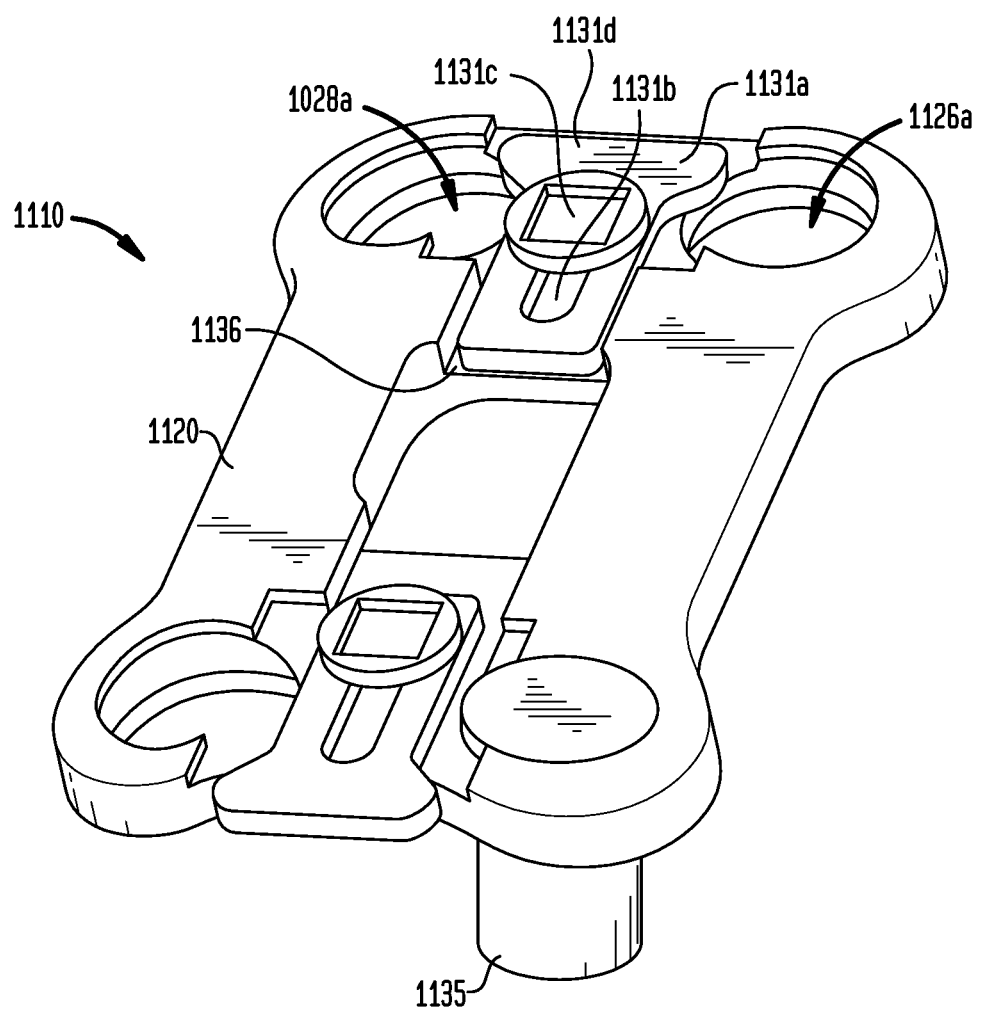
FIG. 27 is a perspective view of a bone plate system in accordance with still a further embodiment of the present invention.

FIG. 27 depicts another embodiment as bone plate system 1110 including bone plate 1120, cover slide 1131a having a transverse end 1131d being its widest portion, and tightener 1131c. Tightener 1131c is rotatably connected to bone plate 1120 and is also disposed through a channel 1131b on cover slide 1131a. As such, cover slide 1131a may slide along bone plate 1120 whereby transverse end 1131d may be positioned over bone holes 1126a and 1128a. Tightener 1131c may be rotatably secured to bone plate 1120 in order to clamp or tighten cover slide 1131*a* with respect to bone plate 1120.

Figure 28:
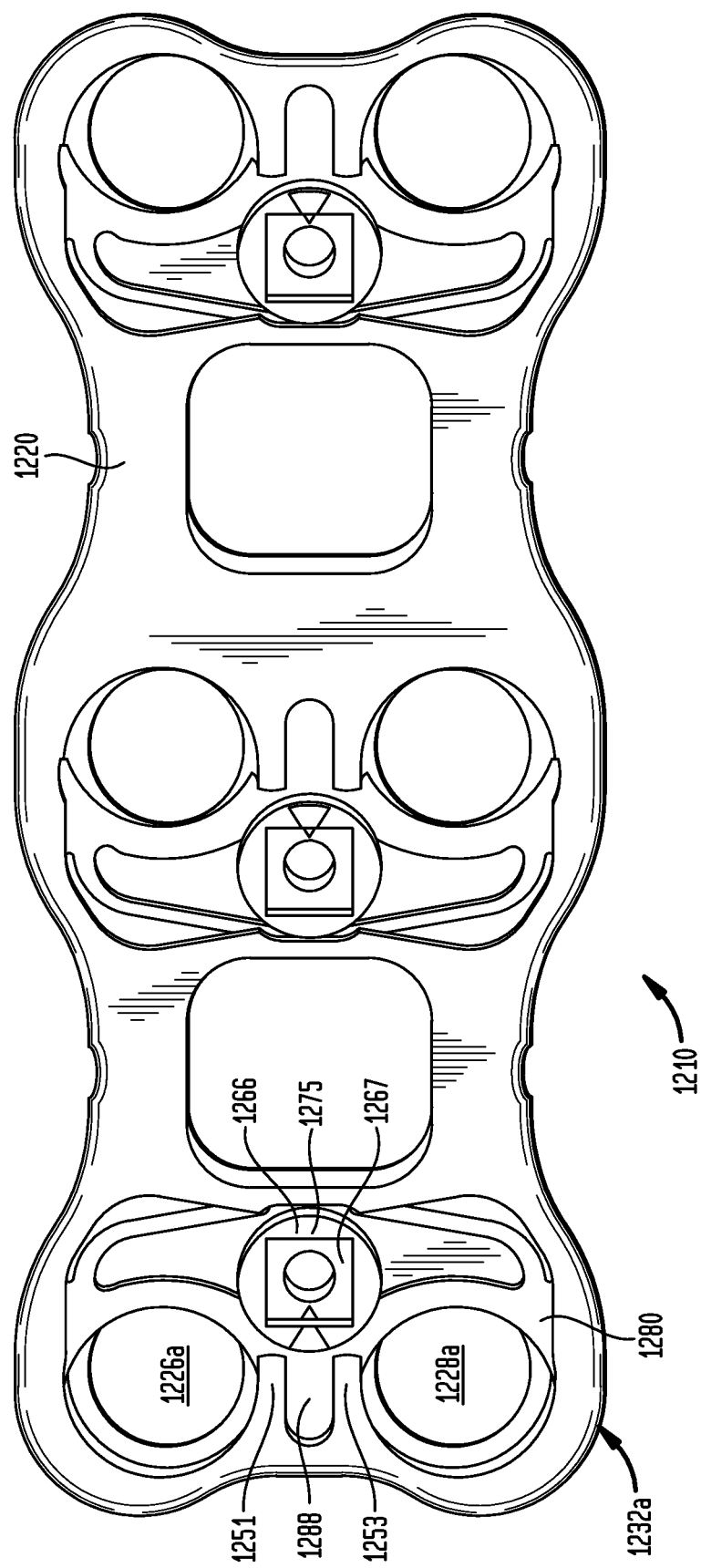
FIG. 28 is a perspective view of a two-level bone plate system in accordance with another embodiment of the present invention.
Figure 29:
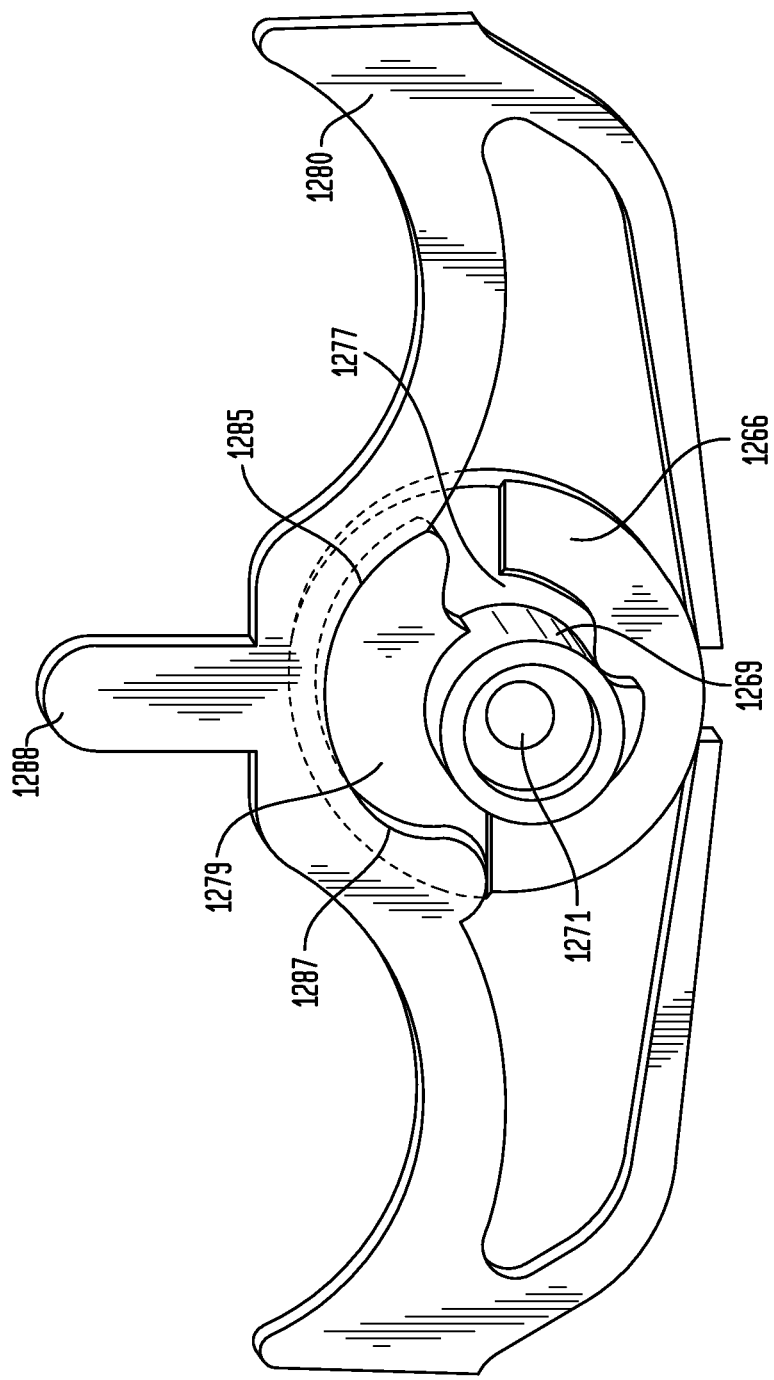
FIG. 29 is a perspective view of the underside of the cam and blocker of the bone plate system of FIG. 28.

Another embodiment is depicted in FIGS. 28 and 29 including a two-level bone plate system 1210. Bone plate 1220 includes cantilever 1254 which is split into first and second projections 1251 and 1253. Absent from bone plate system 1210 is an iteration of central portion 48 of system 10. Instead, bone plate 1220 includes space between first and second projections 1251 and 1253 and central region 1288 of blocker 1280. In this embodiment, central region 1288 extends more broadly between screw hole 1226*a* and 1228*a*.

Cam 1266 is shown in FIGS. 28 and 29 as having a round exterior and a cam recess 1267 shaped to have substantially the same cross section as screw head recess 55. Notably, tool 89 designed to mate with screw head recess 55 may then efficiently be used to also mate with cam recess 1267. Cam 1266 further includes a boss 1269 with a thruhole 1271. Boss 1269 is rotatingly engageable with plate hole 1298 (not shown) of bone plate 1220.

Cam 1266 further includes a top surface 1275, as shown in FIG. 28, and a bottom surface 1277, as shown in FIG. 29. Bottom surface 1277 is configured to rest upon blocker 1280 while also being configured to engage with an edge 1287 of blocker 1280. Bottom surface includes a camming surface 1279 having a curved portion 1285. Camming surface 1279 may be a ramp such that it progressively extends distally from bottom surface 1277 along a clockwise direction (as shown in FIG. 29) of curved portion 1285. As such, as cam 1266 is rotated in a counter-clockwise manner, curved portion 1285 engages edge 1287 of blocker 1280, thereby blocking blocker 1280 from movement in a direction away from pair 1232*a* of screw holes 1226*a* and 1228*a*.

Alternatively, the whole of camming surface 1279 may extend to a certain distal distance from bottom surface 1277 such that ram 1279 is the only portion of cam 1266 disposed distally of bottom surface 1277. In such a configuration, cam 1266 may be rotated such that camming surface 1279 is either engaged or not engaged with blocker 1280.

FIG. 30 depicts an embodiment of bone plate system 1310 similar to that depicted in FIGS. 28 and 29, although cam 1366 includes an alternate configuration of screw head recess 1355. Cam further includes cam projection 1399 which extends over blocker 1366 in a closed position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate comprising:
    a body defining at least one screw hole having a periphery, the screw hole configured to receive a bone screw inserted in a proximal-to-distal direction;
    a blocker having a blocking end for blocking the bone screw, the blocker being predisposed in a blocking position in which the blocking end at least partially overlaps a portion of a head of the bone screw when the head of the bone screw is disposed within the screw hole, the blocker being moveable from the blocking position as it is contacted by the head of the bone screw during insertion of the bone screw into the screw hole, wherein the blocking end is arcuate and substantially matches only a portion of the periphery of the at least one screw hole; and
    a blocker fixation element having a blocking surface, the blocker fixation element being movable between an open orientation in which the blocking surface is arranged away from the screw hole and the blocker can move from the blocking position, and a closed orientation in which the blocking surface is arranged toward the screw hole and the blocker fixation element prevents substantial movement of the blocker from the blocking position,
    wherein during insertion of the bone screw into the screw hole, the blocker is not movable back to the blocking position unless the entire head of the bone screw is disposed distally of the blocker,
    wherein when the head of the bone screw is disposed within the screw hole, the blocker fixation element cannot be moved to the closed orientation unless the head of the bone screw is disposed within the screw hole beyond the blocker, and
    wherein the blocker fixation element includes a projection that extends over the blocker in the closed position.

2. The bone plate of claim 1, wherein the blocker is separate from the body.

3. The bone plate of claim 2, wherein the body includes a recess and the blocker is at least partially in the recess, and the recess is configured such that the blocking end of the blocker is constrained to move only along a single axis.

4. The bone plate of claim 1, wherein the body includes a recess and a cantilever portion extending over at least a portion of the recess, wherein the blocker is at least partially in the recess and at least a portion of the blocker is disposed beneath the cantilever portion.

5. The bone plate of claim 1, wherein the at least one screw hole includes at least two screw holes, and the blocking end of the blocker is configured for blocking two bone screws from further backout of the at least two screw holes, respectively.

6. A system comprising the bone plate of claim 1 and at least one bone screw.

7. The bone plate of claim 1, wherein the blocker fixation element includes an upper surface and a lower surface, the lower surface having a blocking portion extending downwardly therefrom and having the blocking surface.

8. The bone plate of claim 1, wherein the blocker fixation element is configured to engage the blocker in the closed orientation.

9. The bone plate of claim 1, wherein the body includes a recess and the blocker is at least partially in the recess, the body further defines an aperture in the recess, and the blocker fixation element is disposed within and rotatably engaged with the aperture.

10. A bone plate comprising:
    at least one screw hole configured to receive a bone screw;
    a recess defining a recessed surface;
    a cantilever portion extending over at least a portion of the recess;
    a blocker having a blocking end for blocking the bone screw and a bottom surface, wherein the blocker is at least partially in the recess with the bottom surface contacting the recessed surface and at least a portion of the blocker is disposed beneath the cantilever portion, the blocker being predisposed in a blocking position in which a portion of the bottom surface at the blocking end at least partially overlies a portion of the screw hole, the blocker being moveable from the blocking position as it is contacted by a head of the bone screw during insertion of the bone screw into the screw hole; and
    a blocker fixation element having an open orientation at which the blocker can move from the blocking position and a closed orientation, the closed orientation preventing substantial movement of the blocker from the blocking position, wherein when the head of the bone screw is disposed within the screw hole, the blocker fixation element cannot be moved to the closed orientation unless the head of the bone screw is disposed within the screw hole beyond the blocker.

11. The bone plate of claim 10, further defining an aperture in the recess, wherein the blocker fixation element is disposed within and rotatably engaged with the aperture.

12. The bone plate of claim 10, wherein the at least one screw hole includes at least four screw holes spaced from one another such that at least one of the screw holes is configured to align with a vertebral body of a spine and at least one other of the screw holes is configured to align with a different vertebral body of that spine.

13. A bone plate comprising:
at least one screw hole configured to receive a bone screw;
a blocker having a blocking end for blocking the bone screw from further backout of bone should the bone screw begin to back out after implantation, the blocker being predisposed in a blocking position in which the blocking end at least partially overlaps a portion of the screw hole when the head of the bone screw is disposed within the screw hole, the blocker being moveable from the blocking position as it is contacted by a head of the bone screw during insertion of the bone screw into the screw hole; and
a blocker fixation element including an upper surface and a lower surface, the lower surface having a blocking portion extending downwardly therefrom and configured to abut the blocker, the blocker fixation element having an open orientation in which the blocking portion faces away from the blocker and the blocker can move from the blocking position and a closed orientation in which the blocking portion faces the blocker, the closed orientation preventing substantial movement of the blocker from the blocking position;
wherein during insertion of the bone screw into the screw hole, the blocker fixation element is not movable to the closed orientation unless the screw head passes the blocker, thereby revealing that the blocker fixation element is in position to prevent substantial movement of the blocker; and
wherein the blocker fixation element includes a projection that extends over the blocker in the closed position.

14. The bone plate of claim 13, wherein the blocker fixation element is configured to engage the blocker in the closed orientation.

15. The bone plate of claim 13, wherein the blocker fixation element includes a boss extending from the lower surface that has a thruhole, the boss being rotatingly engageable with a thruhole of the bone plate.

16. The bone plate of claim 13, wherein the blocker fixation element has a recess that substantially matches a recess in the head of the screw.

* * * * *